United States Patent
Adams et al.

(10) Patent No.: US 10,244,986 B2
(45) Date of Patent: Apr. 2, 2019

(54) WIRELESS SENSOR PATCHES AND METHODS OF MANUFACTURING

(71) Applicant: Avery Dennison Corporation, Glendale, CA (US)

(72) Inventors: James W. Adams, Mentor, OH (US); Edward A. Armijo, Mentor, OH (US); Ryan Hruska, Concord Township, OH (US); Michael R. Onderisin, Concord Township, OH (US); David Silvestro, Mentor, OH (US)

(73) Assignee: Avery Dennison Corporation, Glendale, CA (US)

( * ) Notice: Subject to any disclaimer, the term of this patent is extended or adjusted under 35 U.S.C. 154(b) by 773 days.

(21) Appl. No.: 14/762,950

(22) PCT Filed: Jan. 23, 2014

(86) PCT No.: PCT/US2014/012734
§ 371 (c)(1),
(2) Date: Jul. 23, 2015

(87) PCT Pub. No.: WO2014/116816
PCT Pub. Date: Jul. 31, 2014

(65) Prior Publication Data
US 2015/0351689 A1 Dec. 10, 2015

Related U.S. Application Data

(60) Provisional application No. 61/755,623, filed on Jan. 23, 2013, provisional application No. 61/755,629, filed on Jan. 23, 2013.

(51) Int. Cl.
*A61B 5/00* (2006.01)
*A61B 5/053* (2006.01)
*A61B 5/0408* (2006.01)

(52) U.S. Cl.
CPC ........ *A61B 5/6833* (2013.01); *A61B 5/04085* (2013.01); *A61B 5/0533* (2013.01); *A61B 2562/12* (2013.01); *Y10T 29/49131* (2015.01)

(58) Field of Classification Search
CPC . A61B 5/6833; A61B 5/0533; A61B 5/04085; A61B 2562/12; H05K 3/0011;
(Continued)

(56) References Cited

U.S. PATENT DOCUMENTS

| 3,646,606 A | 2/1972 | Buxton et al. |
| 3,872,455 A | 3/1975 | Fuller et al. |

(Continued)

FOREIGN PATENT DOCUMENTS

| CN | 101266400 | 9/2008 |
| CN | 102740766 | 10/2012 |

(Continued)

OTHER PUBLICATIONS

The State Intellectual Property Office of P.R.C Search Report issued in corresponding Chinese Application No. 2014800175998, dated Nov. 29, 2017.

(Continued)

*Primary Examiner* — Peter DungBa Vo
*Assistant Examiner* — Kaying Kue
(74) *Attorney, Agent, or Firm* — Avery Dennison Corporation

(57) ABSTRACT

Wireless sensor patches include a skin-friendly adhesive and a flexible cover patch. In further examples, methods of manufacturing a plurality of wireless sensor patches include the step (I) of unwinding a flexible support membrane from a support membrane storage roll along an assembly path. The flexible support membrane is provided with a skin adhesive configured to mount a first face of the flexible support membrane to a skin surface. The method further (Continued)

comprises the step (II) of sequentially mounting a plurality of sensor devices with respect to a second face of the flexible support membrane along a longitudinal axis of the assembly path. The method further includes the step (III) of sequentially separating the flexible support membrane to provide the plurality of wireless sensor patches, wherein each wireless sensor patch includes a corresponding one of the plurality of sensor devices.

8 Claims, 15 Drawing Sheets

(58) Field of Classification Search
CPC ... H05K 3/28; Y10T 29/4902; B32B 2556/00;
B32B 2535/00; B32B 7/12
USPC ............. 29/841, 832; 156/60, 272.2–275.7
See application file for complete search history.

(56) References Cited

U.S. PATENT DOCUMENTS

| | | |
|---|---|---|
| 3,943,918 A | 3/1976 | Lewis |
| 3,949,388 A | 4/1976 | Fuller |
| 3,989,035 A | 11/1976 | Zuehlsdorff |
| 4,121,573 A | 10/1978 | Crovella et al. |
| 4,121,575 A | 10/1978 | Mills et al. |
| 4,233,987 A | 11/1980 | Feingold |
| 4,321,933 A | 3/1982 | Baessler |
| 4,471,354 A | 9/1984 | Smith |
| 4,509,531 A | 4/1985 | Ward |
| 4,583,549 A | 4/1986 | Manoli |
| 4,674,512 A | 6/1987 | Rolf |
| 4,681,118 A | 7/1987 | Asai et al. |
| 4,686,998 A | 8/1987 | Robbins |
| 4,738,674 A * | 4/1988 | Todd ............... A61F 5/485 5/484 |
| 4,817,628 A | 4/1989 | Zealear et al. |
| 4,830,776 A | 5/1989 | Thompson |
| 4,957,109 A | 9/1990 | Groeger et al. |
| 4,981,141 A | 1/1991 | Segalowitz |
| 5,090,410 A | 2/1992 | Saper et al. |
| 5,125,405 A | 6/1992 | Schmid |
| 5,153,584 A | 10/1992 | Engira |
| 5,168,874 A | 12/1992 | Segalowitz |
| 5,191,886 A | 3/1993 | Paeth et al. |
| 5,197,471 A | 3/1993 | Otero |
| 5,228,449 A | 7/1993 | Christ et al. |
| 5,307,263 A | 4/1994 | Brown |
| 5,307,818 A | 5/1994 | Segalowitz |
| 5,400,794 A | 3/1995 | Gorman |
| 5,511,533 A | 4/1996 | Waller |
| 5,511,548 A | 4/1996 | Riazzi et al. |
| 5,634,468 A | 6/1997 | Platt et al. |
| 5,724,025 A | 3/1998 | Tavori |
| 5,790,036 A | 8/1998 | Fisher et al. |
| 5,862,803 A | 1/1999 | Besson et al. |
| 5,868,671 A | 2/1999 | Mahoney |
| 5,879,292 A | 3/1999 | Sternberg et al. |
| 5,899,855 A | 5/1999 | Brown |
| 5,916,157 A | 6/1999 | Crosz |
| 5,957,854 A | 9/1999 | Besson et al. |
| 6,057,758 A | 5/2000 | Dempsey et al. |
| 6,076,002 A | 6/2000 | Cartmell et al. |
| 6,117,077 A | 9/2000 | Del Mar et al. |
| 6,147,618 A | 11/2000 | Halleck et al. |
| 6,149,614 A * | 11/2000 | Dunshee ............... A61F 13/023 206/440 |
| 6,160,478 A | 12/2000 | Jacobsen et al. |
| 6,238,338 B1 | 5/2001 | Deluca et al. |
| 6,289,238 B1 | 9/2001 | Besson et al. |
| 6,307,481 B1 | 10/2001 | Lehrman et al. |
| 6,326,421 B1 | 12/2001 | Lipman |
| 6,336,900 B1 | 1/2002 | Alleckson et al. |
| 6,377,185 B1 | 4/2002 | Halleck et al. |
| 6,385,473 B1 | 5/2002 | Haines et al. |
| 6,398,727 B1 | 6/2002 | Bui et al. |
| 6,415,033 B1 | 7/2002 | Halleck et al. |
| 6,416,471 B1 | 7/2002 | Kumar et al. |
| 6,434,421 B1 | 8/2002 | Taheri |
| 6,438,413 B1 | 8/2002 | Taheri |
| 6,441,747 B1 | 8/2002 | Khair et al. |
| 6,450,953 B1 | 9/2002 | Place et al. |
| 6,453,186 B1 | 9/2002 | Lovejoy et al. |
| 6,494,829 B1 | 12/2002 | New et al. |
| 6,501,386 B2 | 12/2002 | Lehrman et al. |
| 6,577,893 B1 | 6/2003 | Besson et al. |
| 6,579,231 B1 | 6/2003 | Phipps |
| 6,583,220 B1 | 6/2003 | Lipman |
| 6,595,929 B2 | 7/2003 | Stivoric et al. |
| 6,602,191 B2 | 8/2003 | Quy |
| 6,605,038 B1 | 8/2003 | Teller et al. |
| 6,661,347 B2 | 12/2003 | Lehrman et al. |
| 6,690,959 B2 | 2/2004 | Thompson |
| 6,703,939 B2 | 3/2004 | Lehrman et al. |
| 6,710,100 B1 | 3/2004 | Lipman |
| 6,734,802 B2 | 5/2004 | Halleck et al. |
| 6,785,569 B2 | 8/2004 | Schmidt et al. |
| 6,814,706 B2 | 11/2004 | Barton et al. |
| 6,817,979 B2 | 11/2004 | Nihtila |
| 6,847,836 B1 | 1/2005 | Sujdak |
| 6,847,913 B2 | 1/2005 | Wigley et al. |
| 6,864,796 B2 | 3/2005 | Lehrman et al. |
| 6,875,174 B2 | 4/2005 | Braun et al. |
| 6,881,191 B2 | 4/2005 | Oakley et al. |
| 6,897,788 B2 | 5/2005 | Khair et al. |
| 6,936,007 B2 | 8/2005 | Quy |
| 6,947,565 B2 | 9/2005 | Halleck et al. |
| 6,963,772 B2 | 11/2005 | Bloom et al. |
| 6,970,731 B1 | 11/2005 | Jayaraman et al. |
| 6,985,078 B2 | 1/2006 | Suzuki et al. |
| 7,020,508 B2 | 3/2006 | Stivoric et al. |
| 7,032,301 B1 | 4/2006 | Schmidt et al. |
| 7,092,846 B2 | 8/2006 | Vock et al. |
| 7,095,331 B2 | 8/2006 | Lehrman et al. |
| 7,129,836 B2 | 10/2006 | Lawson et al. |
| 7,145,461 B2 | 12/2006 | Lehrman et al. |
| 7,153,262 B2 | 12/2006 | Stivoric et al. |
| 7,156,808 B2 | 1/2007 | Quy |
| 7,161,484 B2 | 1/2007 | Tsoukalis |
| 7,167,743 B2 | 1/2007 | Heruth et al. |
| 7,206,630 B1 | 4/2007 | Tarler |
| 7,215,989 B1 | 5/2007 | Burks |
| 7,215,991 B2 | 5/2007 | Besson et al. |
| 7,223,236 B2 | 5/2007 | Brown |
| 7,261,690 B2 | 8/2007 | Teller et al. |
| 7,264,591 B2 | 9/2007 | Brown |
| 7,285,090 B2 | 10/2007 | Stivoric et al. |
| 7,286,864 B1 | 10/2007 | Schmidt et al. |
| 7,301,452 B2 | 11/2007 | Gerder et al. |
| 7,313,440 B2 | 12/2007 | Miesel |
| 7,335,416 B2 | 2/2008 | Lipman |
| 7,342,491 B2 | 3/2008 | Fujisaava et al. |
| 7,382,247 B2 | 6/2008 | Welch et al. |
| 7,387,607 B2 | 6/2008 | Holt et al. |
| 7,395,106 B2 | 7/2008 | Ryu et al. |
| 7,407,484 B2 | 8/2008 | Korman |
| 7,479,116 B2 | 1/2009 | Yarden |
| 7,479,890 B2 | 1/2009 | Lehrman et al. |
| 7,485,095 B2 | 2/2009 | Shusterman |
| 7,486,980 B2 | 2/2009 | Lin et al. |
| 7,489,959 B1 | 2/2009 | Schmidt et al. |
| 7,502,643 B2 | 3/2009 | Farringdon et al. |
| 7,515,043 B2 | 4/2009 | Welch et al. |
| 7,539,532 B2 | 5/2009 | Tran |
| 7,539,533 B2 | 5/2009 | Tran |
| 7,542,878 B2 | 6/2009 | Nanikashvili |
| 7,558,622 B2 | 7/2009 | Tran |
| 7,597,668 B2 | 10/2009 | Yarden |
| 7,620,439 B2 | 11/2009 | Menon et al. |
| 7,625,117 B2 | 12/2009 | Haslett |
| 7,627,451 B2 | 12/2009 | Vock et al. |
| 7,668,588 B2 | 2/2010 | Kovacs |
| 7,672,703 B2 | 3/2010 | Yeo et al. |

(56) References Cited

U.S. PATENT DOCUMENTS

| | | | |
|---|---|---|---|
| 7,687,678 B2 | 3/2010 | Jacobs | |
| 7,697,999 B2 | 4/2010 | Axelgaard | |
| 7,711,506 B2 | 5/2010 | Burdett et al. | |
| 7,733,224 B2 | 6/2010 | Tran | |
| 7,760,082 B2 | 7/2010 | Wong et al. | |
| 7,761,261 B2 | 7/2010 | Shmueli et al. | |
| 7,769,464 B2 | 8/2010 | Gerber et al. | |
| 7,822,481 B2 | 10/2010 | Gerber et al. | |
| 7,881,764 B1 | 2/2011 | Schmidt et al. | |
| 7,904,133 B2 | 3/2011 | Gehman et al. | |
| 7,905,815 B2 | 3/2011 | Ellis et al. | |
| 7,952,475 B2 | 5/2011 | Ivanov et al. | |
| 7,965,180 B2 | 6/2011 | Koyama | |
| 7,969,307 B2 | 6/2011 | Peeters | |
| 7,981,046 B2 | 7/2011 | Yarden et al. | |
| 8,016,776 B2 | 9/2011 | Bourget et al. | |
| 8,032,206 B1 | 10/2011 | Farazi et al. | |
| 8,032,229 B2 | 10/2011 | Gerber et al. | |
| 8,079,953 B2 | 12/2011 | Braun et al. | |
| 8,094,009 B2 | 1/2012 | Allen et al. | |
| 8,095,209 B2 | 1/2012 | Flaherty | |
| 8,103,333 B2 | 1/2012 | Tran | |
| 8,108,036 B2 | 1/2012 | Tran | |
| 8,116,841 B2 | 2/2012 | Bly et al. | |
| 8,121,673 B2 | 2/2012 | Tran | |
| 8,125,331 B2 | 2/2012 | Allen et al. | |
| 8,126,567 B2 | 2/2012 | Gerber et al. | |
| 8,130,095 B2 | 3/2012 | Allen et al. | |
| 8,135,473 B2 | 3/2012 | Miesel et al. | |
| 8,188,868 B2 | 5/2012 | Case | |
| 8,200,320 B2 | 6/2012 | Kovacs | |
| 8,201,330 B1 | 6/2012 | Rood et al. | |
| 8,204,597 B2 | 6/2012 | Gerber et al. | |
| 8,214,007 B2 | 7/2012 | Baker et al. | |
| 8,242,903 B2 | 8/2012 | Koyama | |
| 8,249,686 B2 | 8/2012 | Libbus et al. | |
| 8,253,547 B2 | 8/2012 | Otto | |
| 8,255,238 B2 | 8/2012 | Powell et al. | |
| 8,277,377 B2 | 10/2012 | Quy | |
| 8,285,356 B2 | 10/2012 | Bly et al. | |
| 8,287,451 B2 | 10/2012 | Hu et al. | |
| 8,303,172 B2 | 11/2012 | Zei et al. | |
| 8,323,188 B2 | 12/2012 | Tran | |
| 8,323,189 B2 | 12/2012 | Tran et al. | |
| 8,328,718 B2 | 12/2012 | Tran | |
| 8,350,708 B2 | 1/2013 | Case | |
| 8,378,811 B2 | 2/2013 | Crump et al. | |
| 8,425,415 B2 | 4/2013 | Tran | |
| 8,428,682 B1 | 4/2013 | Rood et al. | |
| 8,444,578 B2 | 5/2013 | Bourget et al. | |
| 8,446,275 B2 | 5/2013 | Utter | |
| 8,449,471 B2 | 5/2013 | Tran | |
| 8,460,189 B2 | 6/2013 | Libbus et al. | |
| 8,461,988 B2 | 6/2013 | Tran | |
| 8,475,368 B2 | 7/2013 | Tran et al. | |
| 8,500,636 B2 | 8/2013 | Tran | |
| 8,508,360 B2 | 8/2013 | Koyama | |
| 8,525,673 B2 | 9/2013 | Tran | |
| 8,527,213 B2 | 9/2013 | Husheer | |
| 8,529,457 B2 | 9/2013 | Devot et al. | |
| 8,529,811 B2 | 9/2013 | Drysdale et al. | |
| 8,529,841 B2 | 9/2013 | Drucker et al. | |
| 8,531,291 B2 | 9/2013 | Tran | |
| 8,540,644 B2 | 9/2013 | Husheer | |
| 8,548,174 B2 | 10/2013 | Dufresne et al. | |
| 8,562,527 B2 | 10/2013 | Braun et al. | |
| 8,582,421 B2 | 11/2013 | Sloan | |
| 8,614,630 B2 | 12/2013 | Narasimhan et al. | |
| 8,620,402 B2 | 12/2013 | Parker et al. | |
| 8,630,699 B2 | 1/2014 | Baker et al. | |
| 8,653,965 B1 | 2/2014 | Otto et al. | |
| 8,684,900 B2 | 4/2014 | Tran | |
| 8,684,922 B2 | 4/2014 | Tran | |
| 8,688,189 B2 | 4/2014 | Shennib | |
| 8,708,903 B2 | 4/2014 | Tran | |
| 8,708,904 B2 | 4/2014 | Stivoric et al. | |
| 8,718,742 B2 | 5/2014 | Beck et al. | |
| 8,734,339 B2 | 5/2014 | Rao et al. | |
| 8,795,174 B2 | 8/2014 | Manicka et al. | |
| 8,801,577 B2 | 8/2014 | Dibenedetto et al. | |
| 8,814,755 B2 | 8/2014 | Adidas | |
| 8,818,481 B2 | 8/2014 | Bly | |
| 8,852,097 B2 | 10/2014 | Shimada et al. | |
| 8,868,616 B1 | 10/2014 | Otto et al. | |
| 8,903,671 B2 | 12/2014 | Park et al. | |
| 9,782,082 B2 * | 10/2017 | Gannon | A61B 5/002 |
| 2002/0180605 A1 * | 12/2002 | Ozguz | H01L 21/6836 340/573.1 |
| 2003/0125616 A1 * | 7/2003 | Black | A61N 5/1048 600/407 |
| 2003/0149349 A1 | 8/2003 | Jensen | |
| 2005/0065489 A1 | 3/2005 | Driskell et al. | |
| 2005/0261598 A1 | 11/2005 | Banet et al. | |
| 2006/0030781 A1 | 2/2006 | Shennib | |
| 2006/0155183 A1 | 7/2006 | Kroecker et al. | |
| 2006/0224072 A1 | 10/2006 | Shennib | |
| 2006/0290496 A1 * | 12/2006 | Peeters | A61B 5/0002 340/572.1 |
| 2007/0073132 A1 | 3/2007 | Vosch | |
| 2007/0129622 A1 | 6/2007 | Bourget et al. | |
| 2008/0051670 A1 | 2/2008 | Banet et al. | |
| 2008/0275327 A1 | 11/2008 | Faarbaek et al. | |
| 2009/0076363 A1 | 3/2009 | Bly et al. | |
| 2009/0182204 A1 | 7/2009 | Semler et al. | |
| 2009/0318793 A1 | 12/2009 | Datta et al. | |
| 2010/0056881 A1 | 3/2010 | Libbus et al. | |
| 2010/0198044 A1 | 8/2010 | Gehman et al. | |
| 2010/0228113 A1 | 9/2010 | Solosko et al. | |
| 2010/0317958 A1 | 12/2010 | Beck et al. | |
| 2010/0322996 A1 * | 12/2010 | Wibaux | C09J 9/00 424/443 |
| 2011/0144470 A1 * | 6/2011 | Mazar | A61B 5/04085 600/391 |
| 2012/0071731 A1 | 3/2012 | Gottesman | |
| 2012/0071743 A1 * | 3/2012 | Todorov | G06F 19/3481 600/372 |
| 2013/0116532 A1 * | 5/2013 | Brunner | A61B 5/0536 600/390 |
| 2014/0221796 A1 * | 8/2014 | Lia | A61B 5/01 600/324 |

FOREIGN PATENT DOCUMENTS

| | | |
|---|---|---|
| EP | 0612498 | 8/1994 |
| EP | 0877346 | 11/1998 |
| EP | 1871218 | 5/2012 |
| GB | 1056772 | 1/1967 |
| GB | 2323196 | 9/1998 |
| JP | 04161138 | 6/1992 |
| KR | 20090008786 | 1/2009 |
| WO | 2008005016 | 1/2008 |
| WO | 2008097652 | 8/2008 |
| WO | 2010085755 A1 | 7/2010 |
| WO | 2010107913 A1 | 9/2010 |

OTHER PUBLICATIONS

Di Rienzo et al. "A Textile-Based Wearable System for VitalSign Monitoring: Applicability in Cardiac Patients" Computers in Cardiology [Online] 2005, 32, pp. 699-701.

Haahr et al. "A Wearable Electronic Patch for Wireless Continuous Monitoring of Chronically Diseased Patients" Proceedings of the 5th International Workshop on Wearable and Implantable Body Sensor Networks [Online] 2008, pp. 66-70.

Mundt et al. "Multiparameter Wearable Physiologic Monitoring System for Space and Terrestrial Applications" IEEE Transactions on Information Technology in Biomedicine [Online] 2005, 9, pp. 382-391.

Oliver et al. "HealthGear: A Real-time Wearable System for Monitoring and Analyzing Physiological Signals" Microsoft Research Technical Report MSR-TR-2005-182 http://www.nuriaoliver.com/healthGear/healthGear.pdf (accessed Jun. 9, 2011).

(56) References Cited

OTHER PUBLICATIONS

Paradiso et al. "Wearable Health Care System for Vital Signs Monitoring" Studies in Health Technologies and Informatics [Online] 2004, 108, pp. 253-259.

Saenz "The WIN Human Recorder—A Patch to Monitor Your Health" SingularityHub.com http://singularitytees.com/2010/01/27/the_win_human_recorder_a_patch_to_monitor_your_health/ (accessed Jun. 9, 2011).

Saenz "Toumaz Digital Plaster to Wirelessly Monitor Patient Vital Signs Hits Trials" SingularityHub.com http://singularityhub.com/2009/11/09/toumaz-digital-plaster-to-wirelessly-monitor-patient-vital-signs-hits-trials/ (accessed Jun. 9, 2011).

Yilmaz et al. "Detecting Vital Signs with Wearable Wireless Sensors" Sensors [Online] 2010, 10, pp. 10837-10862.

International Preliminary Report on Patentability issued in corresponding International Application No. PCTUS1412734 dated Jul. 28, 2015.

International Search Report and the Written Opinion of the International Searching Authority, or the Declaration, dated Jul. 8, 2014.

\* cited by examiner

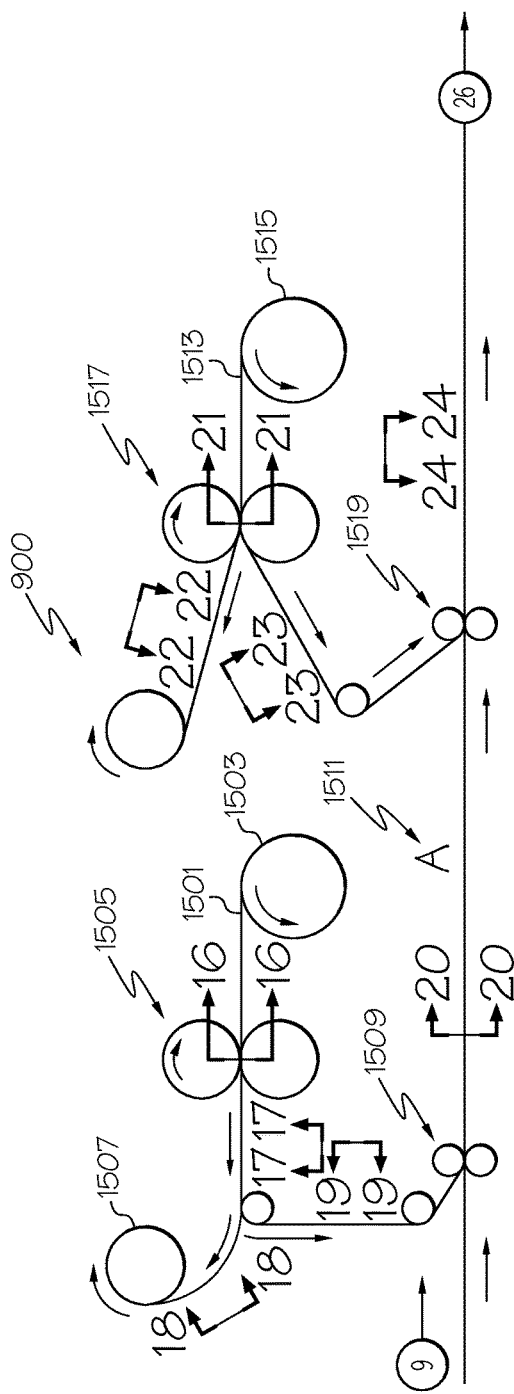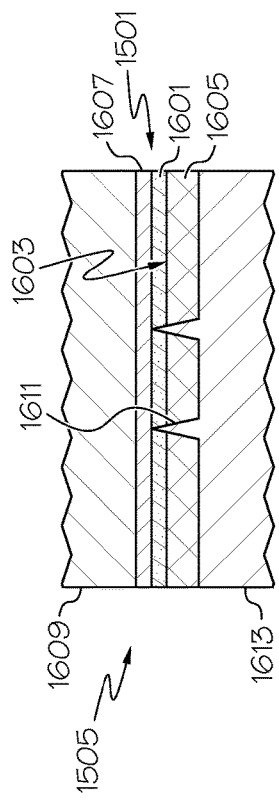

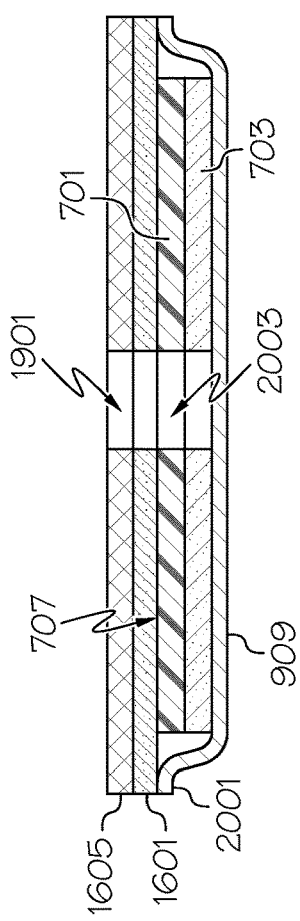
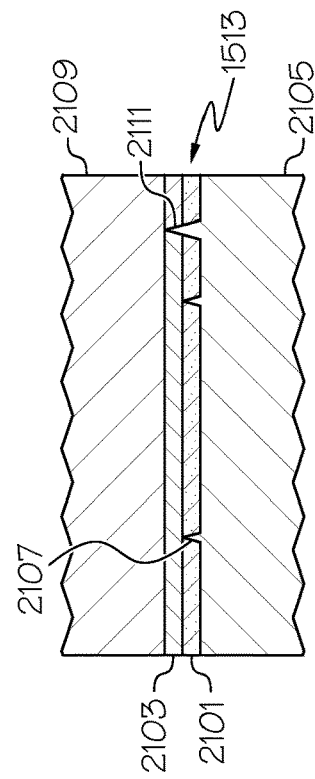
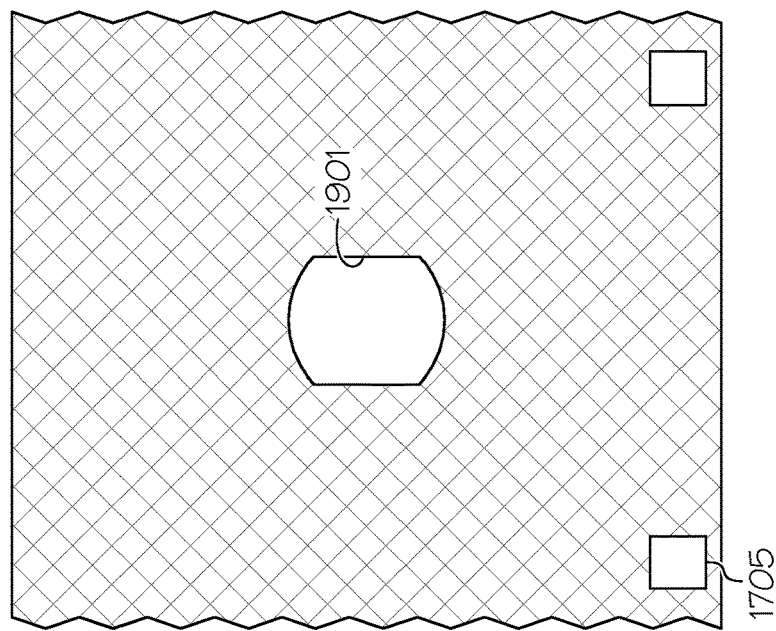

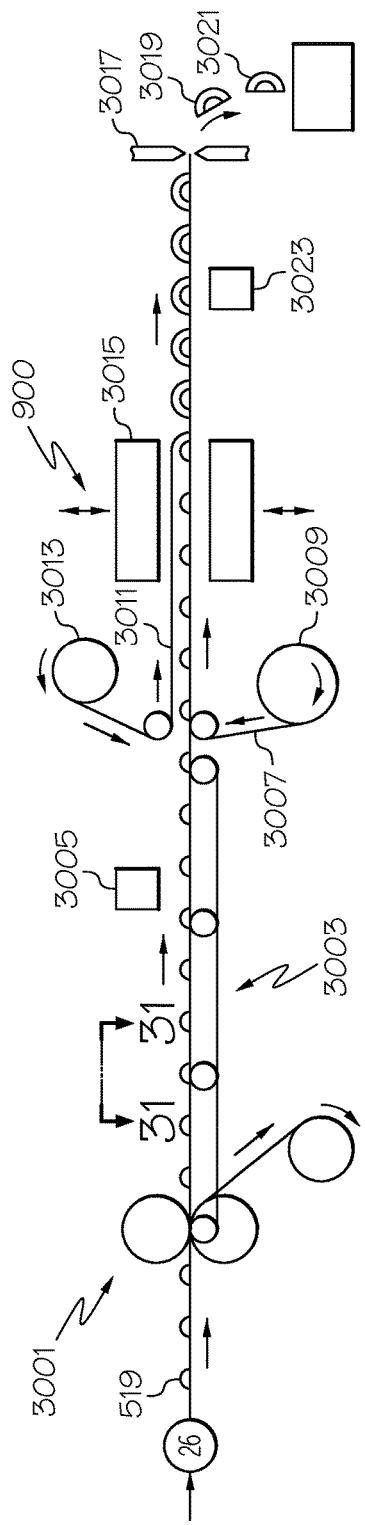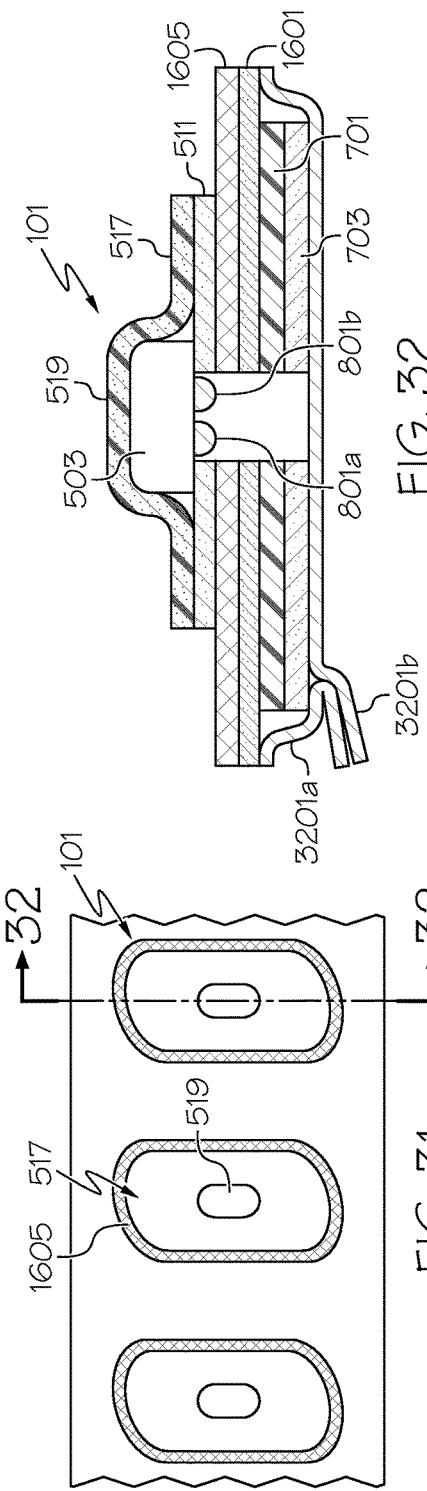

WIRELESS SENSOR PATCHES AND METHODS OF MANUFACTURING

CROSS-REFERENCE TO RELATED APPLICATIONS

The present application is a 371 of International Application No. PCT/US2014/012734, which was published in English on Jul. 31, 2014, which claims the benefit of U.S. Provisional Patent Application No. 61/755,623 filed Jan. 23, 2013 and U.S. Provisional Patent Application No. 61/755,629 filed Jan. 23, 2013, which are incorporated herein by reference in their entireties.

FIELD OF THE INVENTION

The present invention relates to wireless sensor patches and methods of manufacturing and, more particularly, to wireless sensor patches including a flexible support patch and a flexible cover patch and methods of manufacturing a plurality of wireless sensor patches.

BACKGROUND OF THE INVENTION

It is known to sensors to monitor various parameters of a patient. Such sensors may include temperature sensors, Electrocardiogram (ECG) sensors, Galvanic Skin Response (GSR) sensors depending on the application of the sensor. In some applications, the sensors may be attached by wire to a device configured to process and/or display information obtained by the sensors. In further examples, sensors are known to comprise wireless sensors that communicate with another device wirelessly. There is a desire to provide wireless sensor patches to monitor various parameters of a patient. There is also a desire to provide manufacturing methods to sequentially manufacture a plurality of wireless sensor patches in an efficient and cost effective manner.

BRIEF SUMMARY OF THE INVENTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

In a first aspect of the disclosure, a method of manufacturing a plurality of wireless sensor patches comprises the step (I) of unwinding a flexible support membrane from a support membrane storage roll along an assembly path. The flexible support membrane is provided with a skin adhesive configured to mount a first face of the flexible support membrane to a skin surface. The method further comprises the step (II) of sequentially mounting a plurality of sensor devices with respect to a second face of the flexible support membrane along a longitudinal axis of the assembly path. The method further includes the step (III) of sequentially separating the flexible support membrane to provide the plurality of wireless sensor patches, wherein each wireless sensor patch includes a corresponding one of the plurality of sensor devices.

In one example of the first aspect, after step (II) and before step (III), the method further includes the steps of: providing a plurality of flexible cover patches; and attaching each flexible cover patch with respect to the second face of the flexible support membrane such that each of the plurality of sensor devices is at least partially housed within a pocket defined by at least one of the flexible support membrane and the corresponding flexible cover patch. For example, the step of attaching each flexible cover patch can include the steps of applying a tie layer to the second face of the flexible support membrane, and then laminating the flexible cover patch to the second face of the flexible support membrane with the tie layer.

In another example of the first aspect, the method further includes the steps of: unwinding a flexible cover membrane from a flexible cover membrane storage roll; and sequentially separating the plurality of flexible cover patches from the flexible cover membrane. For example, the method can further include the step of forming a plurality of pockets in the flexible cover membrane along a longitudinal axis of the flexible cover membrane, and wherein the step of sequentially separating the plurality of flexible cover patches provides each flexible cover patch with a corresponding one of the pockets for at least partially housing a corresponding one of the sensor devices.

In still another example of the first aspect, step (III) provides the flexible support membrane as a plurality of flexible support patches that are each provided with a corresponding flexible cover patch attached to a second face of the flexible support patch. In one example, a footprint of each flexible support patch is larger than a footprint of the corresponding attached flexible cover patch.

In yet another example of the first aspect, the skin adhesive is provided as a skin-friendly adhesive, for example, a hydrocolloid skin adhesive. In another example, the skin adhesive further includes an adhesive layer applied to the first face of the flexible support membrane. In such examples, the methods may be provided wherein step (I) mounts the skin-friendly adhesive relative to the first face of the flexible support membrane with the adhesive layer. In a further example, step (III) provides the flexible support membrane as a plurality of flexible support patches that are each provided with a patch of the adhesive layer applied to a first face of the flexible support patch. In yet another example, step (I) mounts the skin-friendly adhesive as a plurality of skin-friendly adhesive patches, wherein at least one of the skin-friendly adhesive patches is mounted to the first face of the flexible support patch with the patch of the adhesive layer. In another example, step (I) mounts the at least one of the skin-friendly adhesive patches to the first face of each corresponding flexible support patch such that an outer periphery of the patch of the adhesive layer circumscribes the at least one of the skin-friendly adhesive patches.

In still another example of the first aspect, the method further comprises the step of providing indicia to a portion of each wireless sensor patch containing information that matches information of indicia provided on a corresponding package housing each wireless sensor patch.

In another example of the first aspect, the method further comprises the step of associating indicia of a portion of the wireless sensor patch with a batch of at least one source of assembly materials used to manufacture the wireless sensor patch.

In a further example of the first aspect, a wireless sensor patch is manufactured in accordance with the first aspect discussed above or any of the examples of the first aspect discussed above, wherein the wireless sensor patch comprises a flexible support patch including a first face and a second face with an outer periphery defining a footprint of the flexible support patch. The wireless sensor patch further includes an adhesive layer applied to the first face of the flexible support patch, and a skin-friendly adhesive patch mounted to the first face of the flexible support patch with the adhesive layer. The wireless sensor patch further includes a sensor device mounted to the second face of the flexible support patch, the sensor device including at least one sensor probe aligned with an aperture extending through the flexible support patch. The wireless sensor patch further includes a flexible cover patch mounted to the second face of the flexible support patch, wherein the sensor device is at least partially housed within a pocket defined by at least one of the flexible support patch and the corresponding flexible cover patch. In another example, the wireless sensor patch further includes a tie layer mounting the flexible cover patch to the second face of the flexible support patch. In another example, the wireless sensor patch provides the flexible support patch as a fabric, such as a nonwoven fabric. In further examples, a footprint of the flexible support patch is larger than a footprint of the flexible cover patch. In still further examples, an outer periphery of the adhesive layer circumscribes the skin-friendly adhesive patch. In still further examples, the skin-friendly adhesive patch comprises a hydrocolloid adhesive patch.

The first aspect discussed above may be provided alone or in combination with any one or more of the examples of the first aspect discussed above.

In a second aspect of the disclosure, a method of manufacturing a plurality of wireless sensor patches comprises the step (I) of unwinding a skin-friendly adhesive membrane from a skin-friendly adhesive membrane storage roll. The skin-friendly adhesive membrane includes a substrate sheet carrying a layer of skin-friendly adhesive and a first release liner carried by the layer of skin-friendly adhesive. The layer of skin-friendly adhesive is sandwiched between the first release liner and the substrate sheet. The method further comprises the step (II) of kiss cutting the substrate sheet and the skin-friendly adhesive to the first release liner to define a skin-friendly adhesive patch. The method still further includes the step (III) of unwinding a flexible support membrane from a support membrane storage roll, wherein the flexible support membrane includes a flexible support sheet with a skin adhesive layer applied to a first face of the flexible support sheet and a second release liner carried by the skin adhesive layer with the skin adhesive layer being sandwiched between the second release liner and the flexible support sheet. The method further includes the step (IV) of kiss cutting the flexible support sheet and the skin adhesive layer to the second release liner to define an opening extending through the flexible support sheet and the skin adhesive layer. The method still further includes the step (V) of removing the second release liner to expose the skin adhesive layer. The method also includes the step (VI) of laminating the substrate sheet to the flexible support sheet with the skin adhesive layer of the flexible support membrane. The method also includes the step (VII) of unwinding a tie layer membrane from a tie layer membrane storage roll, wherein the tie layer membrane includes a tie layer carrying a third release liner. The method further includes the step (VIII) of kiss cutting the tie layer to the third release liner to define a tie layer patch and the step (IX) of laminating the tie layer patch to the flexible support sheet. The method also includes the step (X) of cutting at least one probe opening through the tie layer membrane in alignment with the opening defined during step (IV) and the step (XI) of removing the third release liner to expose the tie layer patch laminated to the flexible support sheet. The method further includes the step (XII) of mounting a sensor device with respect to the flexible support membrane with a sensor probe in alignment with corresponding openings defined during steps (IV) and (X). The method also includes the step (XIII) of unwinding a flexible cover membrane from a flexible cover membrane storage roll and the step (XIV) of forming a pocket within the flexible cover membrane. The method further includes the step (XV) of cutting the flexible cover membrane to define a flexible cover patch including the pocket and the step (XVI) of laminating the flexible cover patch to the tie layer patch with the sensor device being at least partially received in the pocket. The method also includes the step (XVII) of cutting the flexible support sheet and the skin adhesive layer to provide a wireless sensor patch.

In one example of the second aspect, step (XVII) provides an outer periphery of the skin adhesive layer circumscribing the skin-friendly adhesive patch.

In another example of the second aspect, the skin-friendly adhesive comprises a hydrocolloid skin adhesive.

In another example of the second aspect, the flexible support membrane comprises a fabric, such as a nonwoven fabric.

In another example of the second aspect, step (XVII) is performed periodically to sequentially produce a plurality of wireless sensor patches.

In still another example of the second aspect, the method includes the step of providing indicia to a portion each wireless sensor patch containing information that matches information of indicia provided on a corresponding package housing each wireless sensor patch.

In still another example of the second aspect, the method further comprises the step of associating indicia of a portion of the wireless sensor patch with a batch of at least one source of assembly materials used to manufacture the wireless sensor patch.

The second aspect may be provided alone or in combination with any one or more of the examples of the second aspect discussed above.

In accordance with a third aspect, a wireless sensor patch comprises a flexible support patch including a first face and a second face with an outer periphery defining a footprint of the flexible support patch. The wireless sensor patch further includes an adhesive layer applied to the first face of the flexible support patch. The wireless sensor patch still further includes a skin-friendly adhesive patch mounted to the first face of the flexible support patch with the adhesive layer, and a sensor device mounted to the second face of the flexible support patch. The sensor device includes at least one sensor probe aligned with an aperture extending through the flexible support patch. The wireless sensor patch further includes a flexible cover patch mounted to the second face of the flexible support patch, wherein the sensor device is at least partially housed within a pocket defined by at least one of the flexible support patch and the corresponding flexible cover patch.

In one example of the third aspect, the wireless sensor patch includes a tie layer mounting the flexible cover patch to the second face of the flexible support patch.

In another example of the third aspect, the flexible support patch comprises a fabric, such as a nonwoven fabric.

In yet another example of the third aspect, a footprint of the flexible support patch is larger than a footprint of the flexible cover patch.

In still another example of the third aspect, an outer periphery of the adhesive layer circumscribes the skin-friendly adhesive patch.

In yet another example of the third aspect, the skin-friendly adhesive patch comprises a hydrocolloid adhesive patch.

The third aspect discussed above may be provided alone or in combination with any one or more of the examples of the third aspect discussed above.

In accordance with a fourth aspect, a wireless sensor patch comprises a printed flexible circuit board and at least one electronic component mounted to the printed flexible circuit board and extending from a first side of the printed flexible circuit board. The wireless sensor patch includes a skin-friendly adhesive patch mounted to a second side of the printed flexible circuit board and a flexible cover patch mounted with respect to the skin-friendly adhesive patch with the electronic component positioned within a space between the flexible cover patch and the skin-friendly adhesive patch. The wireless sensor patch further includes a cushion layer positioned to extend between the electronic component and the flexible cover patch.

In one example of the fourth aspect, the wireless sensor patch further includes a tie layer mounting the skin-friendly adhesive patch to the second side of the printed flexible circuit board.

In yet another example of the fourth aspect, the wireless sensor patch further includes at least one electrode extending from a second side of the printed flexible circuit board and extending through a through aperture defined by the skin-friendly adhesive patch. In one example, an electrode insulation member is positioned within the through aperture defined by the skin-friendly adhesive patch and circumscribes the electrode to prevent contact between the electrode and the skin-friendly adhesive patch. In a further example, the electrode extends through an aperture defined by the electrode insulation member.

In still another example of the fourth aspect, the wireless sensor patch further includes at least a first electrode and a second electrode that each extend from a second side of the printed flexible circuit board and each extend through at least one through aperture defined by the skin-friendly adhesive patch. For instance, the wireless sensor patch can include at least one electrode insulation member positioned within the at least one through aperture of the skin-friendly adhesive to prevent contact between at least one of the electrodes and the skin-friendly adhesive patch. In one example, the electrode insulation member prevents both the first electrode and the second electrode from contacting the skin-friendly adhesive patch. In another example, the electrode insulation member includes a first aperture receiving the first electrode and a second aperture receiving the second electrode.

In another example of the fourth aspect, if the electrode insulation member is provided, the electrode insulation member can optionally be received within a single through aperture defined by the skin-friendly adhesive patch.

In still another example of the fourth aspect, if the electrode insulation member is provided, the electrode insulation member may optionally be 8-shaped.

In another example of the fourth aspect, the flexible cover patch defines a viewing port configured to permit viewing of a portion of the cushion layer through the viewing port of the flexible cover patch. For example, the cushion layer may include indicia that can be viewed through the viewing port of the flexible cover patch.

In another example of the fourth aspect, the cushion layer comprises a fabric. In some examples, the fabric comprises a nonwoven fabric.

In yet another example of the fourth aspect, the flexible cover patch has a footprint that is larger than a foot print of the skin-friendly adhesive patch. For example, an adhesive footprint of the wireless sensor patch can include a skin-friendly adhesive portion defined by the skin-friendly adhesive patch that is circumscribed by a peripheral adhesive portion defined by an adhesive layer of the flexible cover patch.

In still another example of the fourth aspect, the skin-friendly adhesive patch comprises a hydrocolloid adhesive patch.

The fourth aspect discussed above may be provided alone or in combination with any one or more of the examples of the fourth aspect discussed above.

In accordance with a fifth aspect, a wireless sensor patch comprises a printed flexible circuit board and at least one electronic component mounted to the printed flexible circuit board and extending from a first side of the printed flexible circuit board. The wireless sensor patch further includes at least one electrode extending from a second side of the printed flexible circuit board and a skin-friendly adhesive patch mounted to a second side of the printed flexible circuit board. The at least one electrode extends through at least one through aperture defined by the skin-friendly adhesive patch. The wireless sensor patch further includes an electrode insulation member positioned within the through aperture defined by the skin-friendly adhesive patch and circumscribes the electrode to prevent contact between the electrode and the skin-friendly adhesive patch. The wireless sensor patch further includes a flexible cover patch mounted with respect to the skin-friendly adhesive patch with the electronic component positioned within a space between the flexible cover patch and the skin-friendly adhesive patch.

In one example of the fifth aspect, the wireless sensor patch further includes a tie layer mounting the skin-friendly adhesive patch to the second side of the printed flexible circuit board.

In another example of the fifth aspect, the electrode extends through an aperture defined by the electrode insulation member.

In still another example of the fifth aspect, the at least one electrode includes at least a first electrode and a second electrode that each extend from a second side of the printed flexible circuit board and each extend through the least one through aperture defined by the skin-friendly adhesive patch. In one example, the electrode insulation member prevents both the first electrode and the second electrode from contacting the skin-friendly adhesive patch. In another example, the electrode insulation member includes a first aperture receiving the first electrode and a second aperture receiving the second electrode. In another example, the electrode insulation member is received within a single through aperture defined by the skin-friendly adhesive patch. In still another example, the electrode insulation member is 8-shaped.

In a further example of the fifth aspect, the flexible cover patch defines a viewing port configured to permit viewing of a portion of the cushion layer through the viewing port of the flexible cover patch. In one example, the portion of the cushion layer includes indicia that can be viewed through the viewing port of the flexible cover patch.

In still a further example of the fifth aspect, the flexible cover patch has a footprint that is larger than a foot print of the skin-friendly adhesive patch. In one example, an adhesive footprint of the wireless sensor patch includes a skin-friendly adhesive portion defined by the skin-friendly adhesive patch that is circumscribed by a peripheral adhesive portion defined by an adhesive layer of the flexible cover patch.

In another example of the fifth aspect, the skin-friendly adhesive patch comprises a hydrocolloid adhesive patch.

The fifth aspect discussed above may be provided alone or in combination with any one or more of the examples of the fifth aspect discussed above.

Other features and advantages of the present invention will become apparent to those skilled in the art from the following detailed description. It is to be understood, however, that the detailed description of the various embodiments and specific examples, while indicating preferred and other embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

These, as well as other objects and advantages of this invention, will be more completely understood and appreciated by referring to the following more detailed description of the presently preferred exemplary embodiments of the invention in conjunction with the accompanying drawings, of which:

FIG. 15 is a continuation of FIG. 9 illustrating further method steps in the method of manufacturing the plurality of wireless sensor patches;

FIG. 16 is a sectional view along line 16-16 of FIG. 15;

FIG. 19 is a view along line 19-19 of FIG. 15;

FIG. 20 is a sectional view along line 20-20 of FIG. 15;

FIG. 21 is a sectional view along line 21-21 of FIG. 15;

FIG. 30 is a continuation of FIG. 26 illustrating further method steps in the method of manufacturing the plurality of wireless sensor patches;

FIG. 31 is a view along line 31-31 of FIG. 30;

FIG. 32 is a sectional view along line 32-32 of FIG. 31;

DETAILED DESCRIPTION OF THE INVENTION

The present invention is now illustrated in greater detail by way of the following detailed description which represents the best presently known mode of carrying out the invention. However, it should be understood that this description is not to be used to limit the present invention, but rather, is provided for the purpose of illustrating the general features of the invention.

Figure 1:
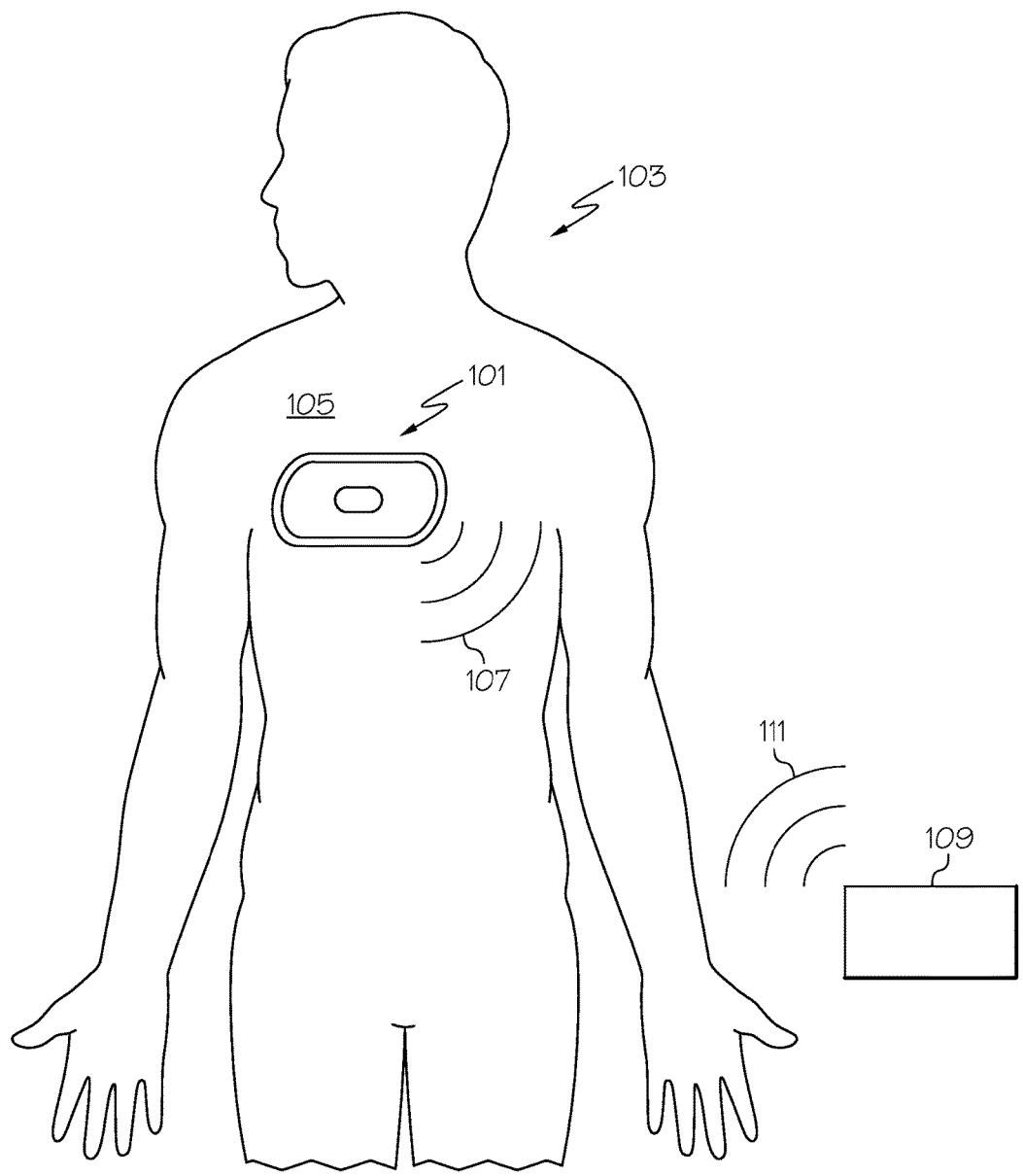
FIG. 1 is example an example wireless sensor patch in accordance with aspects of the disclosure applied to a skin surface of a patient.

FIG. 1 illustrates a wireless sensor patch 101 in accordance with aspects of the present disclosure. The wireless sensor patch 101 can be designed to monitor various parameters of a patient 103. For instance, as shown, the wireless sensor patch 101 may be adhered to a skin surface 105 of the patient 103. Any of the wireless sensor patches discussed throughout the disclosure may be adhered to various alternative skin surfaces of the patient. For instance, the skin patch may be adhered to the chest of a patient (e.g., as shown in FIG. 1), on the arm (e.g., on the back of the arm) of the patient or various other locations of the patient depending on the circumstances.

As discussed below, the wireless sensor patch 101 can include at least one sensor configured to monitor any one or combination of parameters. For instance, the sensor can comprise a Galvanic Skin Response (GSR) sensor configured to detect changes in the resistance of skin to electrical current due to changes in skin perspiration. Measuring the change in skin perspiration can be designed to detect various physiological and/or psychological conditions. In addition or alternatively, one or more Electrocardiogram (ECG) sensors may be provided to monitor the condition of the heart muscle in a patient. In still further examples, the sensors may be designed to detect features of the skin (e.g., temperature, glucose levels, levels of chemicals, pharmaceuticals, etc.). As such, the wireless sensor patch may have a wide range of applications. As discussed below, the wireless skin patch of the present disclosure can allow for comfortable application and monitoring without necessarily requiring a continuous wired connection. Moreover, the wireless sensor patch can be inexpensively produced, thereby rendering the patch potentially disposable. In disposable applications, a new wireless sensor patch to be provided for each application; thereby avoiding expensive sanitation and cleaning procedures.

The wireless sensor patch 101 may include a memory device configured to store data collected by the sensor device. In addition or alternatively, the wireless sensor patch 101 may include a transmitter configured to transmit wireless signals 107 (e.g., by way of Bluetooth wireless technology) to be received by a device 109. The device 109 may be a cell phone or other receiving device that may in turn relay the information by satellite to another location for processing. In further examples, the wireless sensor patch may include a USB port or other interface to allow periodic wired connections with the wireless sensor patch. In such examples, after a period of time, the patient may temporarily provide a wired connection between the patch and the device 109 (e.g., by a USB cable) to provide communication between the device and the wireless sensor patch. In such a manner, information may be gathered by the device 109 continuously (e.g., by a wireless connection) in real time when synced with the device 109 and/or may be periodically sent to the device 109 when the patient makes a wired or other direct connection between the device 109 and the wireless patch. Such wired or wireless connections can be used to download information from the wireless sensor patch to the device 109 such as information gathered from the patient and/or current information about the wireless sensor patch. In further examples, the wired or wireless connection may allow information or commands to be uploaded from the device 109 to the wireless sensor patch. For instance commands may be uploaded to change an operating condition of the patch, to provide information to be displayed by the patch, and/or other functionality.

In further examples, the device 109 may comprise a storage unit configured to store data being transmitted by the wireless sensor patch 101. In further examples, the device 109 may comprise a processing unit configured to process the data. In still further examples, the device 109 may optionally transmit signals 111 configured to be received by the wireless sensor patch 101. For example, the device 109 may send command signals to the wireless sensor patch 101 to change an operating condition of the wireless sensor patch 101.

Figure 2:
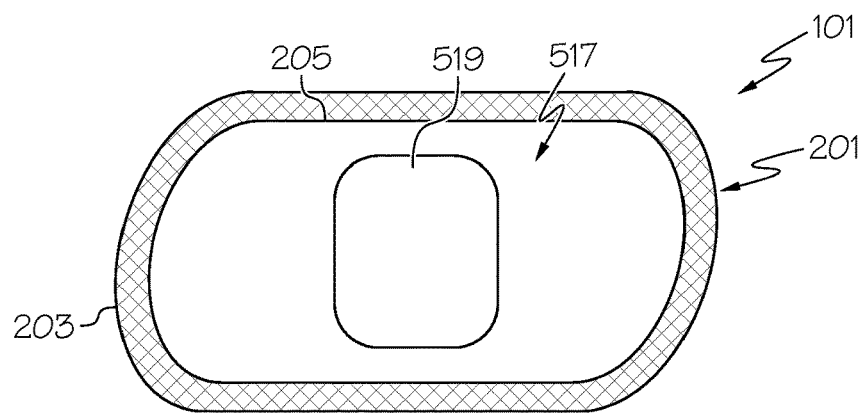
FIG. 2 is a top view of the wireless sensor patch of FIG. 1.
Figure 3:
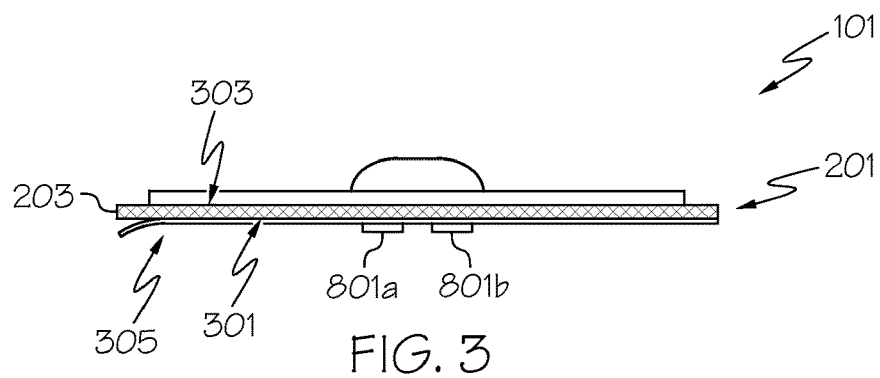
FIG. 3 is a side view of the wireless sensor patch of FIG. 1.
Figure 4:
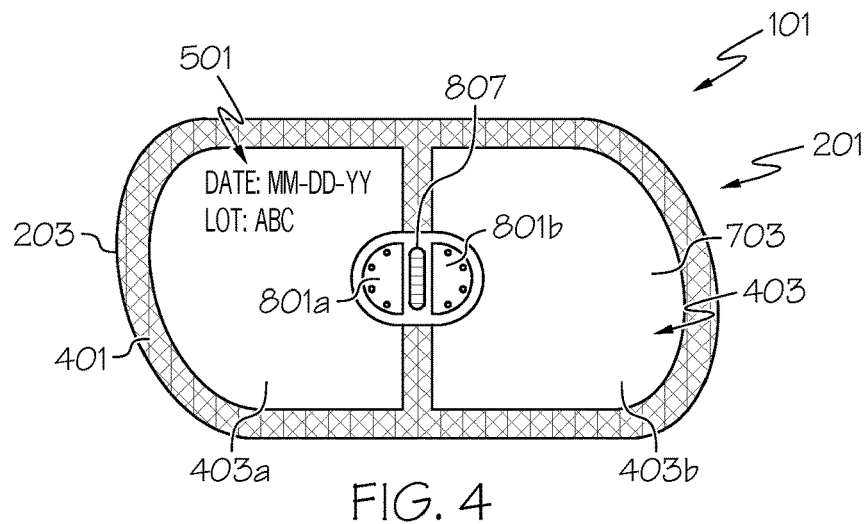
FIG. 4 is a bottom view of the wireless sensor patch of FIG. 1.

FIG. 2 is a top view of the example wireless sensor patch 101 shown in FIG. 1. The wireless sensor patch 101 includes a flexible support patch 201. As shown in FIG. 3, the flexible support patch 201 includes a thickness defined between a first face 301 and a second face 303. As shown in FIGS. 2 and 4, the flexible support patch 201 includes an outer periphery 203 defining a footprint of the flexible support patch 201. The outer periphery 203 can comprise a wide range of shapes and sizes configured to be appropriately attached to the skin surface 105 of the patient 103. The flexible support patch 201 can comprise a wide range of materials configured to provide support while still providing flexibility to allow the wireless sensor patch 101 to conform to a wide range of skin surface shapes. For example, the flexible support patch 201 can comprise a fabric a represented by the cross-hatch pattern illustrated in the drawings. The illustrated fabric comprises a nonwoven fabric although woven fabrics may be provided in further examples.

As represented by the vertical lines set forth in FIG. 4, the wireless sensor patch 101 may also include an adhesive layer 401 applied to the first face 301 of the flexible support patch 201. The adhesive layer can comprise a pressure sensitive adhesive such as rubber-based adhesive, acrylic adhesive or silicone adhesive that allows the patch to immediately adhere to the skin surface 105 upon application of the wireless sensor patch 101. Moreover, the wireless sensor patch 101 can comprise a skin-friendly adhesive patch 403 such as the illustrated first and second skin-friendly adhesive patch portions 403a, 403b mounted to the first face 301 of the flexible support patch 201 with the adhesive layer 401. In one example, the skin-friendly adhesive patch 403 can comprise a hydrocolloid adhesive patch although other skin-friendly adhesives may be provided such as integrated hydrocolloid or other adhesives capable of absorbing moisture. For example, the skin-friendly adhesive patch 403 can comprise a hydrocolloid such as the hydrocolloid material disclosed in any one of U.S. Pat. No. 7,335,416 that issued on Feb. 6, 2008, U.S. Pat. No. 6,710,100 that issued on Mar. 23, 2004, U.S. Pat. No. 6,583,220 that issued on Jun. 24, 2003, U.S. Pat. No. 6,326,421 that issued on Dec. 4, 2001, U.S. patent application Ser. No. 12/866,750 filed Aug. 9, 2010, and U.S. Provisional Patent 61/467,553 filed Mar. 25, 2011, which are herein incorporated by reference in their entireties.

As shown in FIG. 4, an outer periphery of the adhesive layer 401 can circumscribe the skin-friendly adhesive patch 403. As such, an outer peripheral adherence of the wireless sensor patch 101 to the skin surface 105 of the patient 103 may be achieved. At the same time, the skin-friendly adhesive patch 403 may be held in place against the skin surface 105 to allow sufficient time for the skin-friendly adhesive patch 403 to cure into an effective adhesive member. The skin-friendly adhesive patch 403 allows the wireless sensor patch 101 to be applied to the skin surface for a significant length of time without aggravating the skin surface when compared to the adhesive layer 401. At the same time, a relatively small peripheral portion of the adhesive layer 401 may allow the peripheral portions of the patch to be immediately adhered to the skin surface while allowing the skin-friendly adhesive patch 403 sufficient time to cure.

Figure 5:
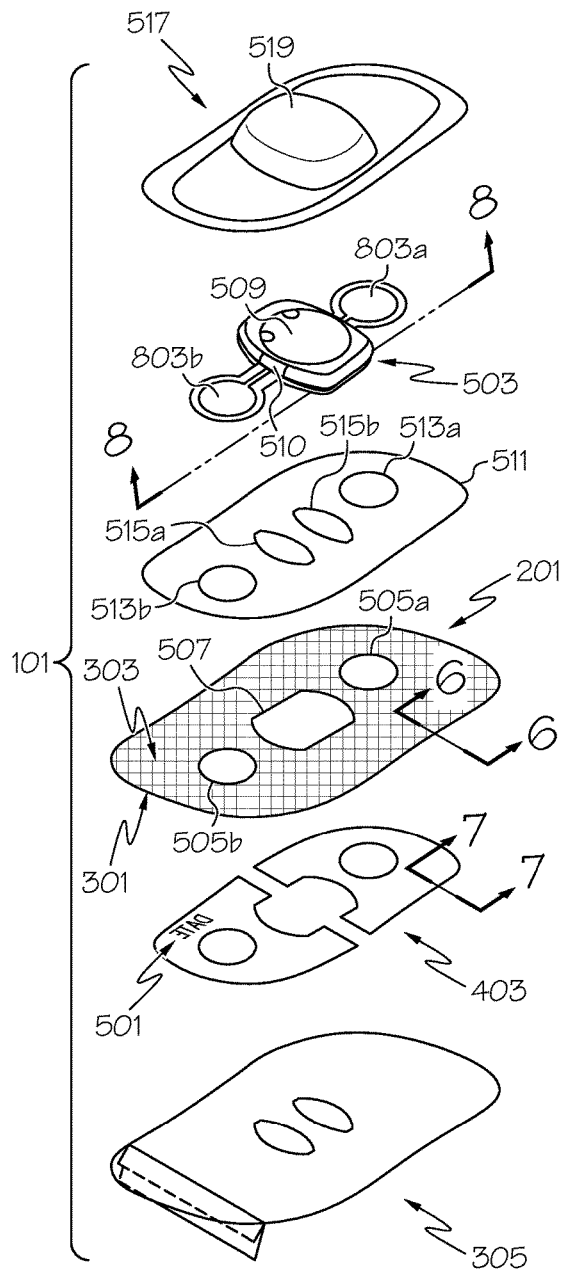
FIG. 5 is an exploded upper perspective view of a wireless sensor patch of FIG. 1.
Figure 6:
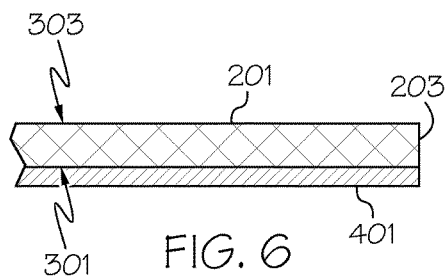
FIG. 6 is a sectional view of the wireless sensor patch along line 6-6 of FIG. 5.
Figure 7:
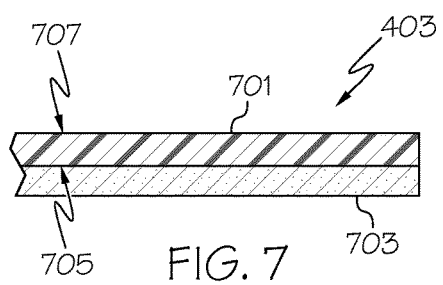
FIG. 7 is a sectional view of the wireless sensor patch along line 7-7 of FIG. 5.

FIG. 5 illustrates an exploded view of the wireless sensor patch 101. FIG. 6 is a cross-sectional view of the flexible support patch 201 demonstrating the adhesive layer 401 being applied to the first face 301 of the flexible support patch 201. FIG. 7 is a cross-sectional view of the skin-friendly adhesive patch 403 along line 7-7 of FIG. 5. As shown, the skin-friendly adhesive patch 403 can include a flexible substrate 701 with a skin-friendly adhesive layer 703 applied to a first face 705 of the flexible substrate 701. In some examples, the flexible substrate 701 can comprise a transparent or translucent substrate 701 to allow viewing of indicia 501 that may be printed on the second face 707 of the flexible substrate (e.g., see FIGS. 4 and 5). In such examples, the indicia 501 may be printed in reverse such that the information may be deciphered by viewing the indicia through the skin-friendly adhesive layer and the flexible substrate 701. The skin-friendly adhesive layer 703 can comprise a hydrocolloid adhesive or other skin-friendly adhesive that can facilitate adhesion to the skin surface for long periods of time relatively low aggravation to the skin layer.

Figure 8:
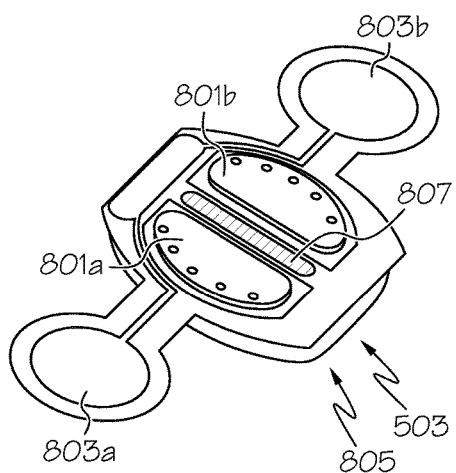
FIG. 8 is a bottom perspective view of a sensor device of the wireless sensor patch of FIG. 5.

As further illustrated in FIG. 5, the wireless sensor patch 101 further includes a sensor device 503. FIG. 5 illustrates a top perspective view of one example sensor device 503 while FIG. 8 illustrates a bottom perspective view of the sensor device 503 along line 8-8 of FIG. 5. As shown in FIG. 8, the sensor device 503 can include a pair of Galvanic Skin Response (GSR) sensor probes 801a, 801b configured to interact with the skin surface 105 to detect changes in the resistance of skin to electrical current due to changes in skin perspiration. The sensor device 503 can also include a pair of Electrocardiogram (ECG) sensor probes 803a, 803b configured to monitor the condition of the heart muscle in a patient.

An electronics module 805 may be provided that can receive signals from the pair of GSR sensor probes 801a, 801b and/or the pair of ECG sensor probes 803a, 803b. In some examples, the wireless sensor patch 101 may only be configured to operate with one of the sensor types although both sensor types may be configured to operate in further examples. For instance, as shown in FIG. 4, only the GSR sensor probes 801a, 801b extend through the flexible support patch 201 to engage the skin surface of the patient. The ECG sensor probes 803a, 803b are not exposed to interact with the skin surface and/or the electronics within the electronic module 805 may be arranged to turn off the ECG sensor and/or may not have ECG sensor functionality. FIG. 5 demonstrates an example where apertures 505a, 505b are provided in the flexible support patch 201 in addition to a central aperture 507 to allow communication of the GSR sensor probes 801a, 801b and the ECG sensor probes 803a, 803b through the flexible support patch 201.

As further shown in FIG. 8, the sensor device 503 can also include identification indicia 807 such as a UPC code or the like to refer to the specific sensor device 503 or a type of sensor device. Referring back to FIG. 5, the sensor device 503 can also include a battery 509 configured to power the sensor device 503 and a control button 510 configured to operate the sensor device. The sensor device 503 can be mounted to the second face 303 of the flexible support patch 201 such that at least one of the sensor probes is aligned with the apertures. Indeed, as shown, the GSR sensor probes 801a, 801b are aligned with the central aperture 507 extending through the flexible support patch. Such alignment allows a portion of the GSR sensor probes 801a, 801b to protrude from the central aperture 507 as shown in FIG. 3. Moreover, as shown in FIG. 5, the ECG sensor probes 803a, 803b may be aligned with the corresponding apertures 505a, 505b extending through the flexible support patch 201. Although not shown, a hydrogel or conductive agent may also be provided to help achieve coupling of the ECG sensor probes 803a, 803b with the skin surface 105 through the corresponding apertures 505a, 505b.

The sensor device 503 may be mounted to the second face 303 of the flexible support patch 201 with various adhesive configurations. For instance, as shown in FIG. 5, adhesive in the form of a tie layer patch 511 can be provided to help mount the sensor device 503 to the second face 303 of the flexible support patch 201. As shown, apertures 513a, 513b may be provided in alignment with the ECG sensor probes 803a, 803b to facilitate appropriate interaction with the skin surface 105. Likewise, apertures 515a, 515b may be provided in alignment with the GSR sensor probes 801a, 801b to facilitate appropriate interaction with the skin surface 105. In some examples, the tie layer may be transparent and/or translucent to allow viewing of the identification indicia 807 from below as shown in FIG. 4.

The wireless sensor patch 101 further includes a flexible cover patch 517 mounted to the second face 303 of the flexible support patch 201 wherein the sensor device 503 is at least partially housed within a pocket 519 defined by at least one of the flexible support patch 201 and the flexible cover patch 517. For example, a protruding portion of the electronic module 805 can be housed within a preformed pocket 519 of the flexible cover patch 517. In some designs, the control button 510 may be activated by depressing a side portion of the flexible preformed pocket 519. The flexible cover patch may comprise a polymeric member, such as a closed cell foam material that may be substantially water resistant to help protect the electrical components of the electronic module 805. As shown, the tie layer patch 511 may function to mount the flexible cover patch 517 to the second face 303 of the flexible support patch 201.

As further illustrated in FIG. 2, the flexible cover patch 517 includes an outer periphery 205 defining a footprint of the flexible cover patch 517. As shown, in one example, the footprint of the flexible support patch 201 defined by the outer periphery 203 of the flexible support patch 201 is larger than a footprint of the flexible cover patch 517. Providing the flexible cover patch 517 with a larger footprint can help prevent overlapping of the periphery 205 of the flexible cover patch 517 that may provide a peeling point. As such, the wireless sensor patch 101 can be securely applied to the skin surface 105 with a reduced chance of inadvertent peeling of the wireless sensor patch 101 from the skin surface 105.

Referring to FIGS. 3 and 5, a release liner 305 may be provided to help preserve the adhesive layer 401 and the skin-friendly adhesive layer 703 from adhering to other surfaces and/or contamination prior to application of the wireless sensor patch.

The wireless sensor patch 101 shown in FIGS. 1-6 may be easily applied to the skin surface 105 of a patient 103. As shown in FIGS. 3 and 5, the release liner 305 may be initially removed to expose the adhesive layer 401 and the skin-friendly adhesive layer 703 as shown in FIG. 4. Moreover, as shown in FIG. 4, the indicia 501 may be read through the skin friendly adhesive. Moreover, the indicia 807 associated with the sensor device 503 may be read through the tie layer patch 511. Next, the wireless sensor patch 101 may be applied to the skin surface 105 of a patient 103 at an appropriate location. Once applied, the outer peripheral portion of the adhesive layer 401 immediately mounts the wireless sensor patch 101 in place, wherein, after sufficient time, the skin-friendly adhesive layer 703 cures to provide the primary bonding while reducing irritation and/or aggravation to the skin layer that may otherwise occur over long periods of time with only the relatively harsh adhesive layer 401.

Various methods may be used to manufacture the wireless sensor patch 101. For example, referring to FIG. 5, the method can include the step of providing the flexible support patch 201 including the first face 301 and the second face 303 with the outer periphery 203 defining the footprint of the flexible support patch 201. The method can also include providing the adhesive layer 401 to the first face 301 of the flexible support patch 201. In further examples, the skin-friendly adhesive patch 403 may be mounted to the first face 301 of the flexible support patch 201 with the adhesive layer 401. In one example, indicia 501 may be printed in reverse on the surface being adhered to the adhesive layer 401. As such, the indicia may be viewed through the skin-friendly adhesive patch 403 as shown in FIG. 4.

Referring back to FIG. 5, the method of manufacturing the skin patch can further include the step of mounting the sensor device 503 to the second face 303 of the flexible support patch 201. At least one sensor probe of the sensor device can be aligned with an aperture extending through the flexible support patch prior to mounting the sensor device to the second face of the flexible support patch. For example, as shown in FIG. 5, the GSR sensor probes 801a, 801b can be aligned with the central aperture 507 of the flexible support patch 201. Likewise, the ECG sensor probes 803a, 803b may be aligned with the corresponding apertures 505a, 505b extending through the flexible support patch 201.

The method of manufacturing can further include the step of mounting the flexible cover patch 517 to the second face 303 of the flexible support patch 201. In one example, the tie layer patch 511 or other adhesive may be used to mount the flexible cover patch 517 to the second face 303 of the flexible support patch 201. After mounting the flexible cover patch 517, the protruding portion of the electronic module 805 is at least partially housed within the pocket 519 defined by the flexible cover patch 517. Although not shown, in addition or alternatively, the flexible support patch 201 may include a pocket for at least a portion of the sensor device 503.

The efficiency and speed of manufacturing the wireless sensor patch may be enhanced by various methods of manufacturing a plurality of wireless sensor patches, for example, sequentially manufacturing a plurality of the wireless sensor patches.

Figure 9:
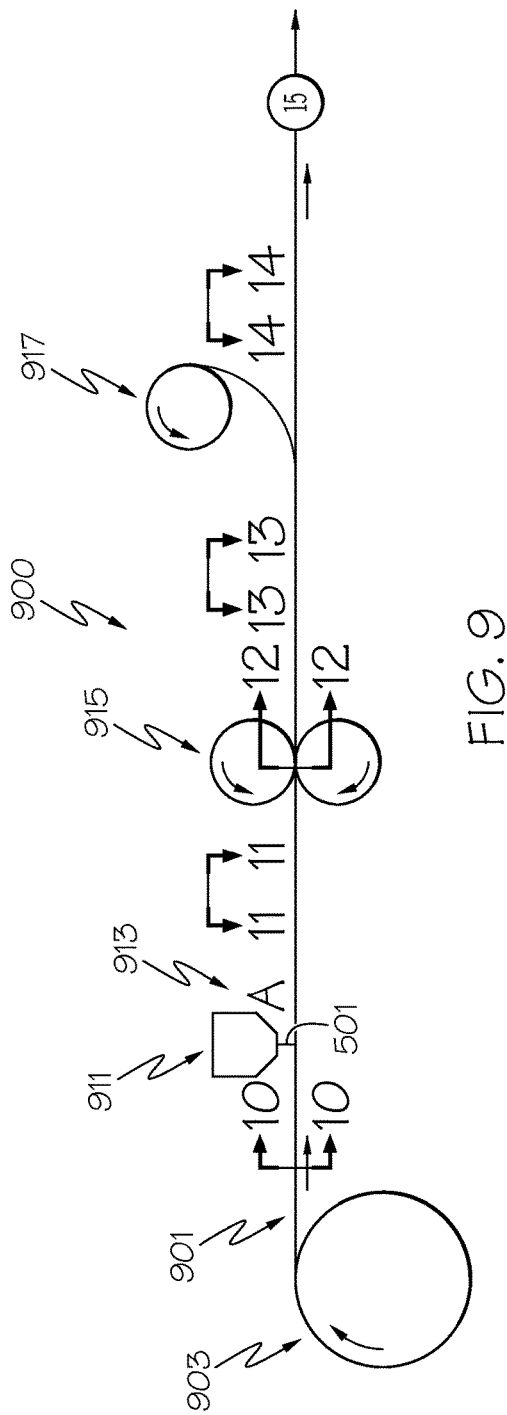
FIG. 9 illustrates method steps in a method of manufacturing a plurality of wireless sensor patches.

FIG. 9 illustrates a schematic view of a manufacturing apparatus 900 demonstrating example method steps of manufacturing a plurality of wireless sensor patches. The method can include the step of unwinding a skin-friendly adhesive membrane 901 from a skin-friendly adhesive membrane storage roll 903.

Figure 10:
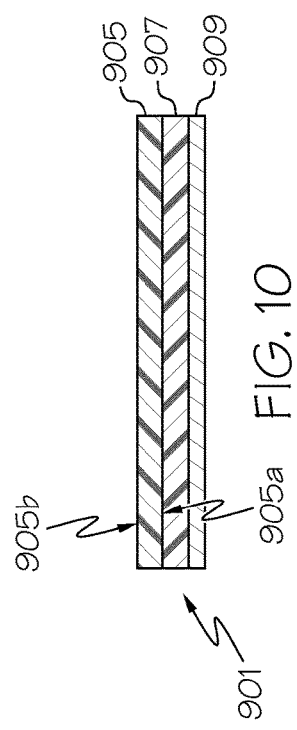
FIG. 10 is a sectional view along line 10-10 of FIG. 9.

As shown in FIG. 10, the skin-friendly adhesive membrane 901 can include a substrate sheet 905 carrying a layer of skin-friendly adhesive 907 on a first face 905a of the substrate sheet 905. The substrate sheet 905 will eventually be separated (e.g., cut) into the flexible substrate 701 of the skin-friendly adhesive patch 403 discussed above. As such, in some examples, the substrate sheet 905 can comprise a transparent or translucent substrate sheet to allow viewing of indicia 501 that may be subsequently printed on the second face 905b of the substrate sheet 905. In some examples, the substrate sheet 905 can comprise a sheet of flexible polyurethane that acts as a carrier sheet for the skin-friendly adhesive 907.

As discussed previously, the skin-friendly adhesive membrane 901 further includes a layer of skin-friendly adhesive 907 that may be carried by the first face 905a of the substrate sheet 905. The skin-friendly adhesive layer 907 will eventually be processed into the skin-friendly adhesive layer 703 of the skin-friendly adhesive patch 403 discussed above. As such, the skin-friendly adhesive layer 907 can comprise a hydrocolloid adhesive or other skin-friendly adhesive that can facilitate adhesion to the skin surface for long periods of time relatively low damage to the skin layer. As further illustrated in FIG. 10, the skin-friendly adhesive membrane 901 can further include a first release liner 909 carried by the layer of skin-friendly adhesive 907. In one example, the first release liner 909 can comprise a siliconized release liner that can protect the skin-friendly adhesive 907 during transport while allowing easy removal of the release liner from contacting the skin-friendly adhesive 907 to expose the skin-friendly adhesive for further processing.

Figure 11:
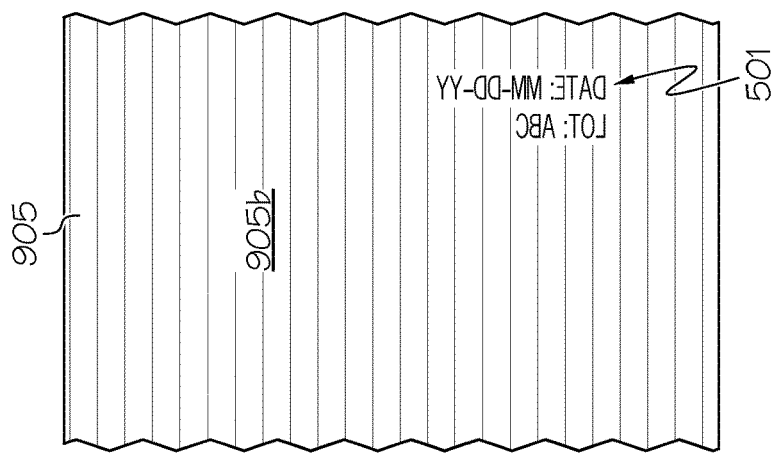
FIG. 11 is a view along line 11-11 of FIG. 9.

The manufacturing apparatus 900 can further include a printing device 911 configured to print indicia 501 on the second face 905b of the substrate sheet 905. As shown in FIG. 11, the indicia may be printed in reverse such that the information may be deciphered by viewing the indicia through the skin-friendly adhesive layer and the flexible substrate through the first face 905a of the substrate sheet 905. The indicia may comprise information relating to the wireless sensor patch 101 such as the date of printing, the lot number and may even include identification information to allow individualized naming of each corresponding wireless sensor patch. The manufacturing apparatus 900 may also include a quality check, such as an optical reader 913 configured to check the printing quality of the indicia 501.

Figure 12:
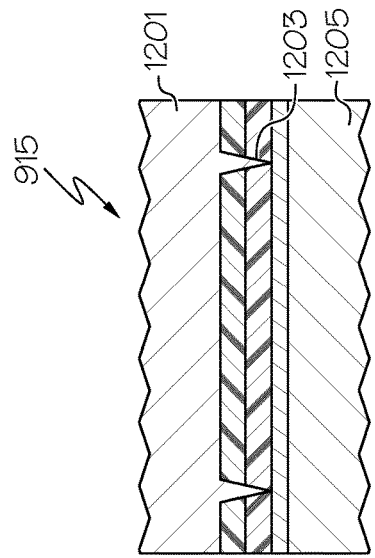
FIG. 12 is a sectional view along line 12-12 of FIG. 9.
Figure 13:
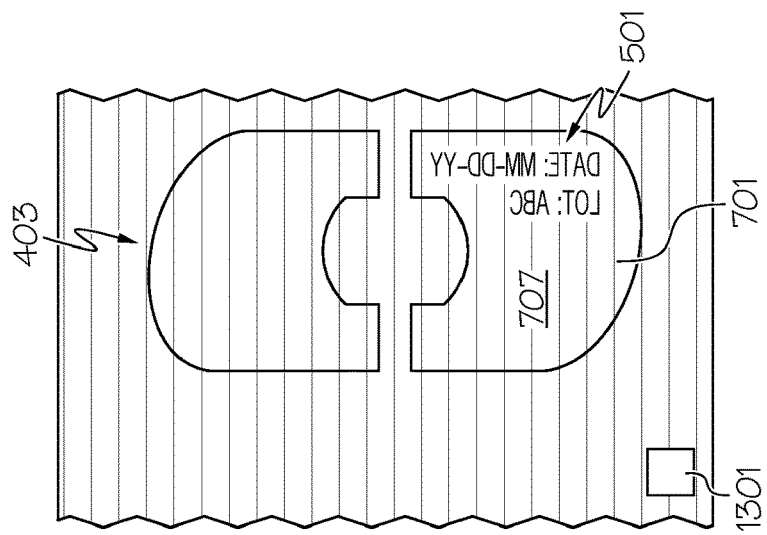
FIG. 13 is a view along line 13-13 of FIG. 9.

The manufacturing apparatus 900 can also include a pair of rollers 915 configured to kiss cut the substrate sheet 905 and the skin-friendly adhesive 907 to the first release liner 909 to define the skin-friendly adhesive patch 403 shown in FIG. 5. Indeed, as shown in FIG. 12, one roller 1201 of the pair of rollers 915 can include a cutting knife 1203 in the shape of the skin-friendly adhesive patch 403. As shown, the cutting knife 1203 is designed to work against an anvil roller 1205 to kiss cut the substrate sheet 905 and the skin-friendly adhesive 907 to the first release liner 909 without cutting through the release liner. As shown in FIG. 13, the shape of the skin-friendly adhesive patch 403 is subsequently kiss cut within the skin-friendly adhesive membrane 901. Once the kiss cut is complete, the indicia 501 may be appropriately located on the second face 707 of the flexible substrate 701 of the skin-friendly adhesive patch 403.

As further illustrated in FIG. 13, a plurality of first registration openings 1301 may be provided by another knife of the pair of rollers (not shown). As shown, the first registration openings 1301 is created by a removed cut-out of the substrate sheet 905, the skin-friendly adhesive 907 and the first release liner 909 of the skin-friendly adhesive membrane 901. The cut-out may be provided periodically along the length of the skin-friendly adhesive membrane 901 (e.g., between each adjacent pair of kiss-cut skin-friendly adhesive patches 403 to facilitate registration of subsequent material layers as discussed more fully below.

Figure 14:
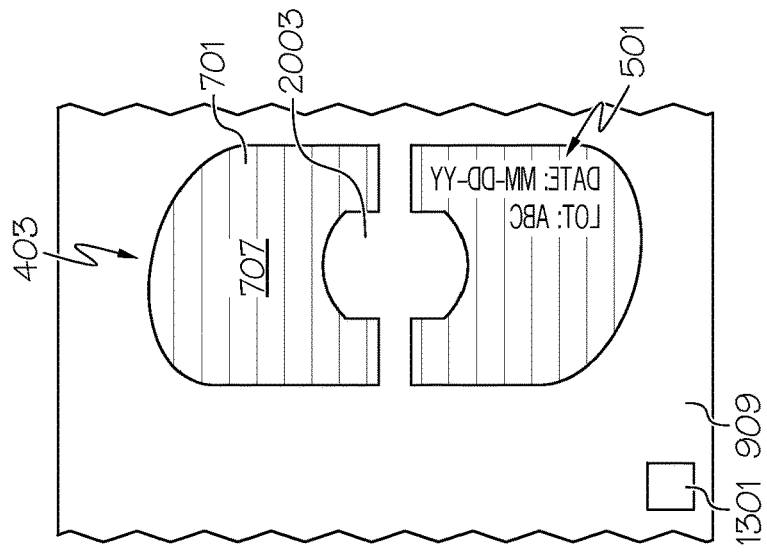
FIG. 14 is a view along line 14-14 of FIG. 9.

Turning back to FIG. 9, the manufacturing apparatus 900 may further include a take up roll 917 configured to wind up unused portions of the skin-friendly adhesive membrane 901 from the first release liner 909. As shown in FIG. 14, the kiss-cut skin-friendly adhesive patches 403 are thereafter left behind on the first release liner 909.

FIG. 15 is a continuation of FIG. 9 illustrating further method steps. The method can further include the step of unwinding a flexible support membrane 1501 from a support membrane storage roll 1503 along an assembly path. As shown in FIG. 16, the flexible support membrane 1501 is provided with a skin adhesive layer 1601 applied to a first face 1603 of a flexible support sheet 1605. The skin adhesive layer 1601 may eventually be cut into the skin adhesive layer 401 of the flexible support patch 201 shown in FIG. 5 and/or FIG. 6. As such, the skin adhesive 1601 may comprise a contact adhesive that may quickly mount the flexible support patch 201 to a skin surface 105. The skin adhesive layer 1601 is therefore configured to adhere to a first face 1603 of the flexible support sheet 1605 such that the skin adhesive may be configured to adhere the first face 1603 of the flexible support sheet 1605 to a skin surface 105. The flexible support sheet 1605 may be eventually cut into the flexible support patch 201. As such, the flexible support sheet 1605 may comprise a fabric, such as a nonwoven fabric although other materials may be used in further examples.

As further illustrated in FIG. 16, the flexible support membrane 1501 may further include a second release liner 1607 carried by the skin adhesive layer 1601 with the skin adhesive layer 1601 being sandwiched between the second release liner 1607 and the flexible support sheet 1605. The second release liner 1607 may comprise a siliconized liner or other release liner configured to preserve the skin adhesive layer 1601 while further processing techniques are carried out as discussed more fully below.

The method can further include the step of kiss cutting the flexible support sheet 1605 and the skin adhesive layer 1601 to the second release liner 1607 to define an opening 1901 (see FIG. 19) extending through the flexible support sheet 1605 and the skin adhesive layer 1601. For example, as shown in FIG. 15, the manufacturing apparatus 900 can also include a pair of rollers 1505 configured to kiss cut the flexible support sheet 1605 and the skin adhesive layer 1601 to the second release liner 1607. As shown in FIG. 16, one roller 1613 of the pair of rollers 1505 can include a cutting knife 1611 in the shape of the opening 1901. As shown, the cutting knife 1611 is designed to work against an anvil roller 1609 to kiss cut the flexible support sheet 1605 and the skin adhesive layer 1601 to the second release liner 1607 without cutting through the second release liner. Once complete, as shown in FIG. 17, a peripheral cut 1701 circumscribes a central tab 1703 in the shape of the opening 1901.

Figure 17:
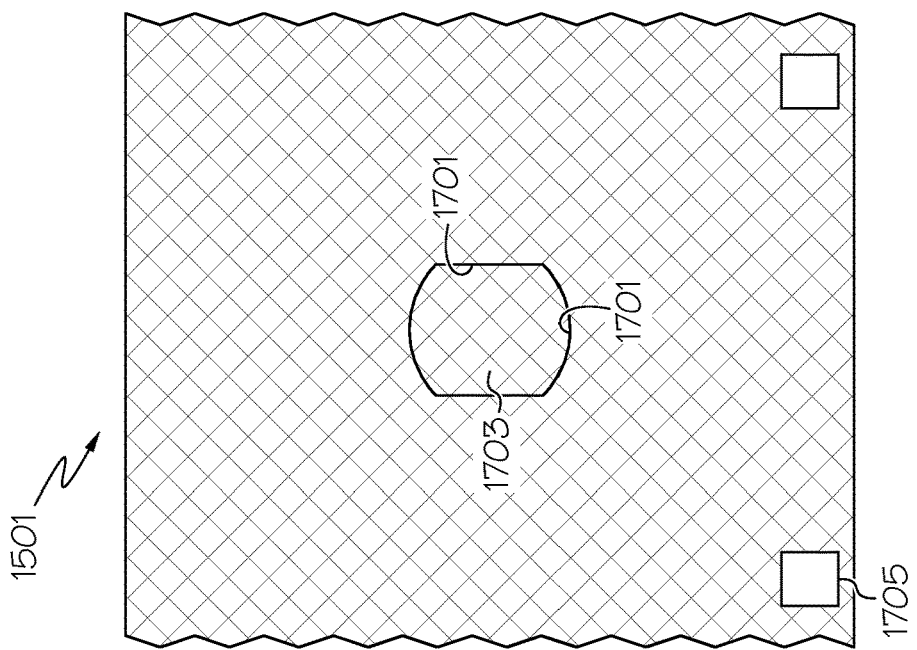
FIG. 17 is a view along line 17-17 of FIG. 15.

Further, as illustrated in FIG. 17, a plurality of second registration openings 1705 may be provided by another knife (not shown) of the pair of rollers 1505. As shown in FIG. 17, the second registration openings 1705 are created by a removed cut-out of the flexible support membrane 1501. The cut-out may be provided periodically along the length of the flexible support membrane to confirm registration between the material layers as discussed more fully below.

Figure 18:
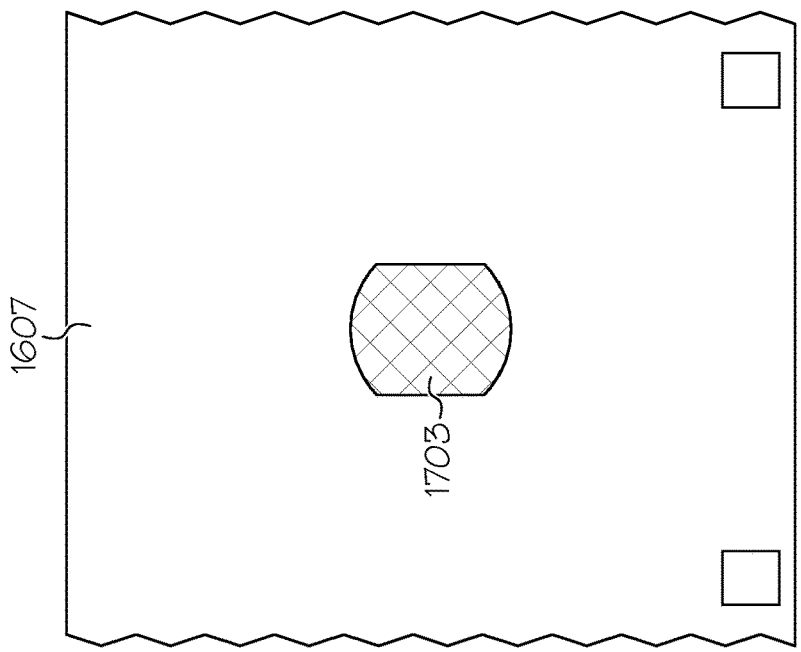
FIG. 18 is a view along line 18-18 of FIG. 15.

Turning back to FIG. 15, the manufacturing apparatus 900 may further include a take up roll 1507 configured to wind up the second release liner 1607 with the central tab 1703 being carried away with the second release liner 1607 as shown in FIG. 18. As such, the second release liner 1607 is removed to expose the skin adhesive layer 601. As shown in FIG. 19, the flexible support sheet 1605 is then carried in a path toward the first release liner 909 wherein the skin adhesive layer 601 is laminated by rollers 1509 to the second face 707 of the flexible substrate 701 of the skin-friendly adhesive patch 403.

FIG. 20 is a sectional view of the flexible support sheet 1605 being mounted to the second face 707 of the flexible substrate 701 of the skin-friendly adhesive patch 403 by way of the skin adhesive layer 1601. As with the other figures, the thicknesses of the layers in FIG. 20 are exaggerated for clarity. As further illustrated in FIG. 20, the outer portions 2001 of the first release liner 909 are temporarily attached to the skin adhesive layer 1601. Once mounted, the opening 1901 of the flexible support sheet 1605 is aligned with the opening 2003 defined within a central portion of the skin friendly adhesive patch (see FIG. 14).

Turning back to FIG. 15, a sensor 1511 such as the optical sensor can monitor the process to ensure proper alignment between the flexible support sheet 1605 and the first release liner 909. If proper registration is achieved, the plurality of first registration openings 1301 are aligned with the plurality of second registration openings 1705. The sensor 1511 can determine appropriate alignment of each corresponding pair of the registration openings 1301, 1705 to confirm appropriate registration and mounting of the flexible support sheet 1605 relative to the skin-friendly adhesive patch 403.

Figure 23:
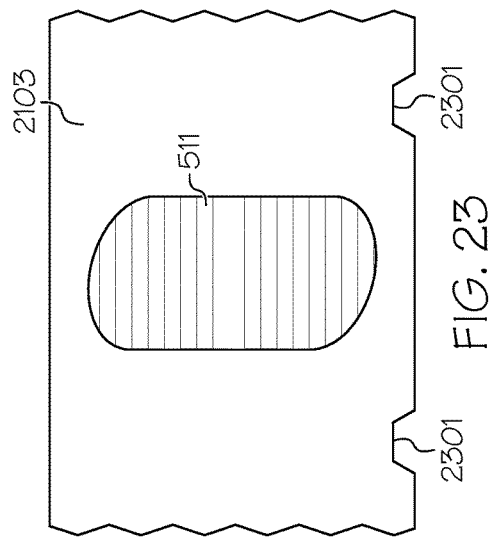
FIG. 23 is a view along line 23-23 of FIG. 15.
Figure 22:
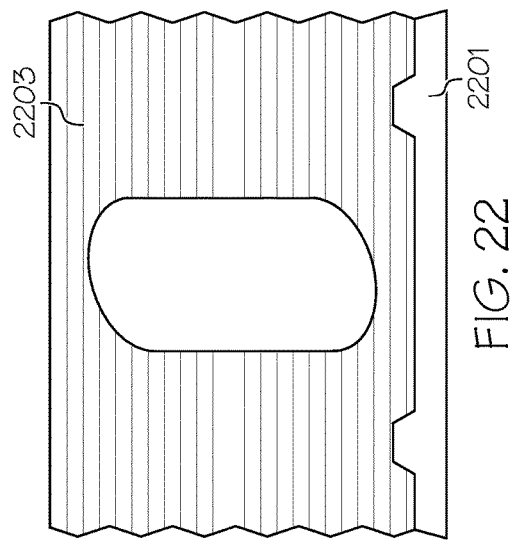
FIG. 22 is a view along line 22-22 of FIG. 15.
Figure 24:
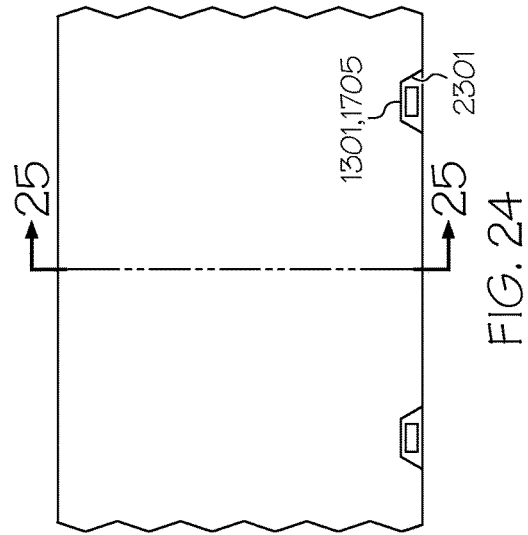
FIG. 24 is a view along line 24-24 of FIG. 15.
Figure 25:
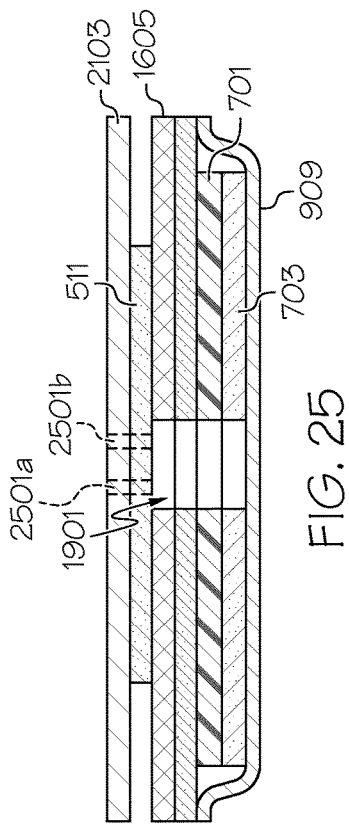
FIG. 25 is a sectional view along line 25-25 of FIG. 24.

As shown in FIG. 15, the manufacturing apparatus 900 may further provide for the step of unwinding a tie layer membrane 1513 from a tie layer membrane storage roll 1515. As shown in FIG. 21, the tie layer membrane 1513 can include a tie layer 2101 carrying a third release liner 2103. As further shown in FIGS. 15 and 21, the manufacturing apparatus 900 can also include a pair of rollers 1517 configured to kiss cut the tie layer 2101 to the third release liner 2103 to define the tie layer patch 511 shown in FIG. 5. As shown in FIG. 21, one roller 2105 of the pair of rollers 1517 can include a cutting knife 2107 in the shape of the outer periphery of the tie layer patch 511. The cutting knife 2107 is designed to work against an anvil roller 2109 to kiss cut the tie layer 2101 to the third release liner 2103 without cutting through the third release liner. At the same time, an edge die cut knife 2111 can trim an edge 2201 of the third release liner 2103 to follow with unused portions of the tie layer as shown in FIG. 22. As shown in FIG. 23, the remainder of the third release liner 2103 carries the tie layer patch 511 cut from the tie layer 2103 of the tie layer membrane 1513. The third release liner 2103 carries the tie layer patch 511 to be laminated by rollers 1519 to the flexible support sheet 1605 as shown in FIGS. 24 and 25. The remainder of the third release liner 2103 can include periodic cut outs 2301 that can provide an alignment check as shown in FIG. 24 (e.g., by an optical sensor or the like).

Figure 26:
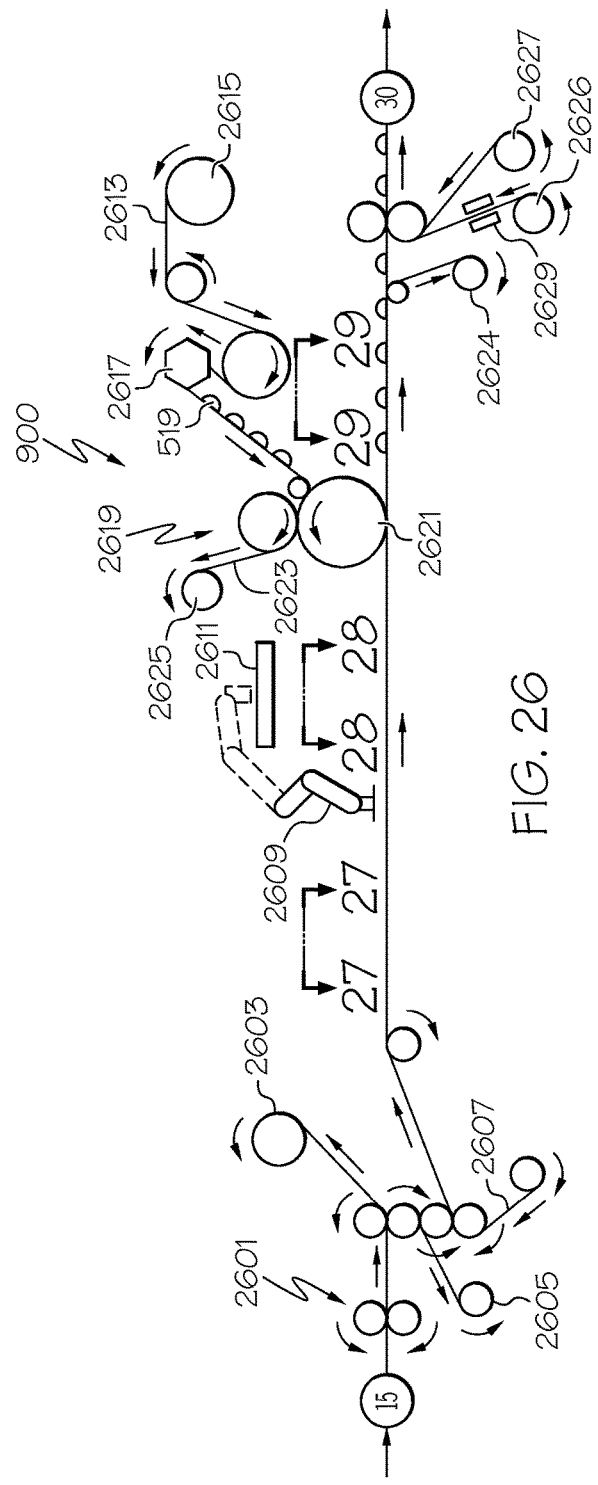
FIG. 26 is a continuation of FIG. 15 illustrating further method steps in the method of manufacturing the plurality of wireless sensor patches.
Figure 27:
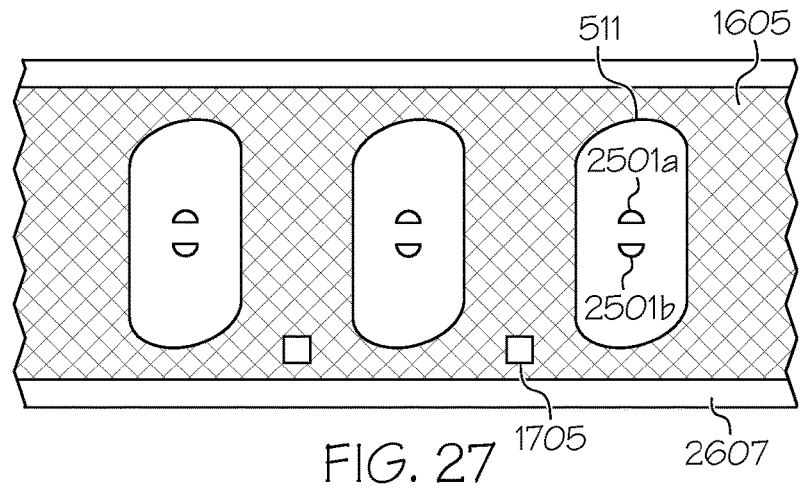
FIG. 27 is a view along line 27-27 of FIG. 26.

FIG. 26 is a continuation of FIG. 15 illustrating further method steps in the method of manufacturing the plurality of wireless sensor patches 101. FIG. 26 illustrates a pair of rollers 2601 configured to die cut at least one probe opening through the tie layer membrane in alignment with the opening 1901. For example, as shown in dashed lines in FIG. 25, the pair of rollers 2601 may cut GSR probe openings 2501a, 2501b through the third release liner 2103 and the die layer patch 511. The method can then include the step of removing the third release liner 2103 for being stored on take up roller 2603. Once the third release liner 2103 is removed, the tie layer patch 511 laminated to the flexible support sheet 1605 is exposed. Next, the first release liner 909 can be removed and stored on take up roller 2605. In place of the first release liner 909, a clear support substrate 2607 may be applied to the skin friendly adhesive layer 907. The result top view is shown in FIG. 27 wherein the tie layer patches 511 are spaced apart in series form one another with GSR probe openings 2501a, 2501b extending through the tie layer patches 511.

Figure 28:
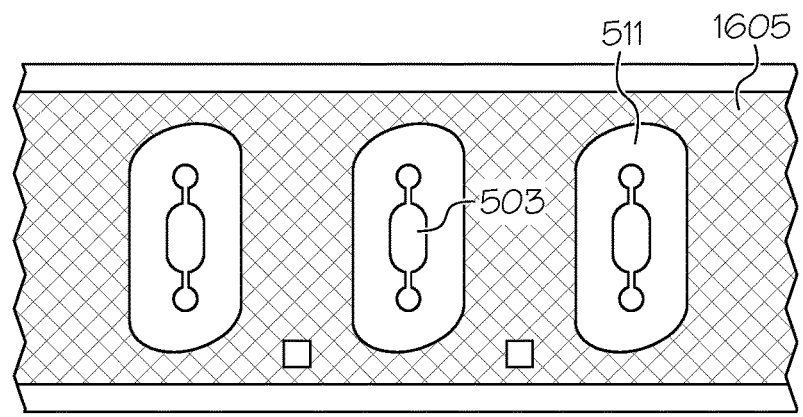
FIG. 28 is a view along line 28-28 of FIG. 26.

Turning back to FIG. 26, a robot 2609 may pick one of a plurality of sensor devices 503 from a source of sensor devices 2611 and mount each sensor device 503 with respect to the flexible support sheet 1605 with the GSR probes 801a, 801b extending through respective GSR probe openings 2501a, 2501b within the tie layer patch 511. A sensing device, such as a camera may view the sensor device 503 prior to placement to achieve proper positioning of the sensor device 503 as shown in FIG. 28.

Figure 29:
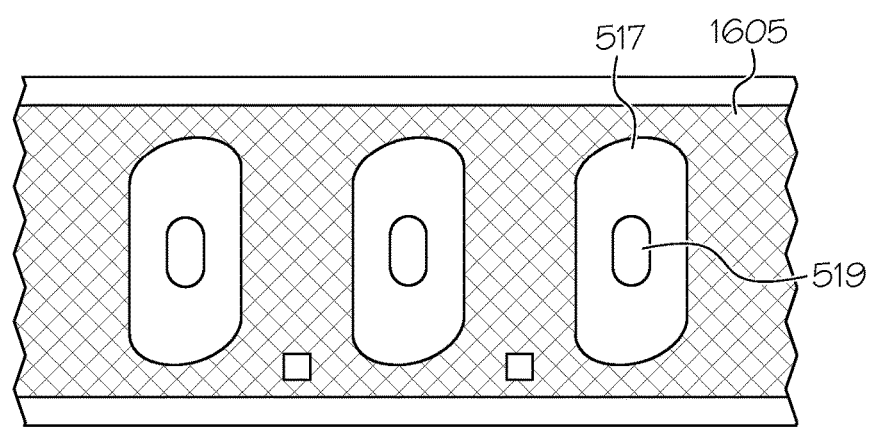
FIG. 29 is a view along line 29-29 of FIG. 26.

The flexible cover patch 517 may then be created and properly positioned over the tie layer patch 511 as discussed with reference to FIGS. 26 and 29. For example, as shown in FIG. 26, the method may include the step of unwinding a flexible cover membrane 2613 from a flexible cover membrane storage roll 2615. The flexible cover membrane 2613 may be heated and then a vacuum formed pocket may be generated by way of vacuum forming cylinder 2617 that includes a plurality of cavities that may suction the heated flexible cover membrane 2613 to form the pockets 519 in the flexible cover membrane 2613. A pair of die cutting rollers 2619 may then cut the flexible cover patches 517 from the flexible cover membrane 2613. Each cut flexible cover patch 517 includes a corresponding one of the pockets 519. Suction within a transfer cylinder 2621 transports the flexible cover patches 517 to be placed in alignment over a corresponding tie layer patch 511. In fact, as shown in FIG. 29, the footprint of the flexible cover patch 517 maybe substantially the same or slightly greater than or less than the footprint of the tie layer patch 511. Unused portions 2623 may be stored by take up roll 2625. In one example, the transfer cylinder 2621 may also act to laminate the flexible cover patch 517 to the tie layer patch 511 with the sensor device being at least partially received in the pocket 519.

As further illustrated in FIG. 26, the clear support substrate 2607 may be removed from the skin friendly adhesive layer 703 and stored in take-up roller 2624. Final release liners (e.g., siliconized release liners) may then be added by release liner rolls 2626, 2627. A folding device 2629 may be provided to provide a J-fold in one of portion of the release liner with the other release liner applied over the J-fold portion. As such, the release liner can comprise to portions 3201a, 3201b (see FIG. 32) to allow easy removal of the release liner when applying the wireless sensor patch to the skin surface 105 of the patient 103.

FIG. 30 is a continuation of FIG. 26 illustrating further method steps in the method of manufacturing the plurality of wireless sensor patches 101. A pair of die cut rollers 3001 operates to cut the flexible support sheet 1605, the skin adhesive layer 1601 and the first and second portions 3201a, 3201b to provide the final wireless sensor patch 101 illustrated in FIGS. 31 and 32. Optionally, a conveyor 3003 may transport the wireless sensor patches 101 to be tested at testing station 3005. The testing station 3005 may activate the wireless sensor patch (i.e., by depressing control button 510) to determine proper functioning of the wireless sensor patch 101. If proper function is not observed, the wireless sensor patch may be marked as defective for later removal from the final batch of wireless sensor patches 101.

As further illustrated in FIG. 30, the method may conclude with a packaging process. As shown, the conveyor can transport the wireless sensor patches 101 on a base substrate 3007 being unwound from a storage roll 3009. A top packaging sheet 3011 can likewise be unwound from a storage roll 3013. Next, a sealing mechanism 3015 may periodically seal off a plurality of the wireless sensor patches 101 in a series of connected pouches that are subsequently separated from one another with a separation device 3017. Once separated, the packaged devices 3019 can be stored in a storage bin 3021.

A printing device 3023 may be designed to print indicia including information relating to the wireless sensor patch 101 on the outside of the package. For example, the indicia 501 on the skin friendly adhesive patch 403 and/or the indicia 807 on the sensor device 503 may contain information that matches the information of indicia provided on a corresponding package housing each wireless sensor patch. Providing the information on the package can be helpful to determine information about the wireless sensor device contained within the package without having to open the package to retrieve the information from the indicia printed on the wireless sensor patch. Moreover, once the wireless sensor device is removed from the packaging, the information is not lost with the packaging since equivalent indicia is also provided on the wireless sensor patch 101.

The method can also determine if any devices were marked as defective by the testing station 3005. If so marked, the defective packaged devices 3019 may be removed prior after being separated and before entering the storage bin. For example, defective packaged devices 3019 may be stored within a defective storage bin (not shown) for subsequent processing or disposal. Still further, in some examples, the method can include the step of associating indicia of a portion of the wireless sensor patch (e.g., indicia 501 and/or indicia 807) with a batch of at least one source of assembly materials used to manufacture the wireless sensor patch. As such, one can easily cross reference material rolls with the particular wireless sensor devices including material from specific rolls. For example, the method can associate each storage roll of material with the particular wireless sensor patch produced. As an example, the information associated with the wireless sensor patch can be used to determine exactly which skin friendly membrane storage roll was used, and other rolls of materials. In such examples, wireless sensor patches may be quickly located that were made from various sources of assembly materials. Such information may be useful to recall certain wireless sensor patches that were made from a defective source of material.

The methods disclosed herein provide multiple repeating steps positioned along an assembly path that may be performed periodically to sequentially produce the plurality of wireless sensor patches 101. Manufacturing the sensor patches continuously from rolls of material can reduce assembly time and costs while providing consistently high quality wireless sensor patches.

Figure 33:
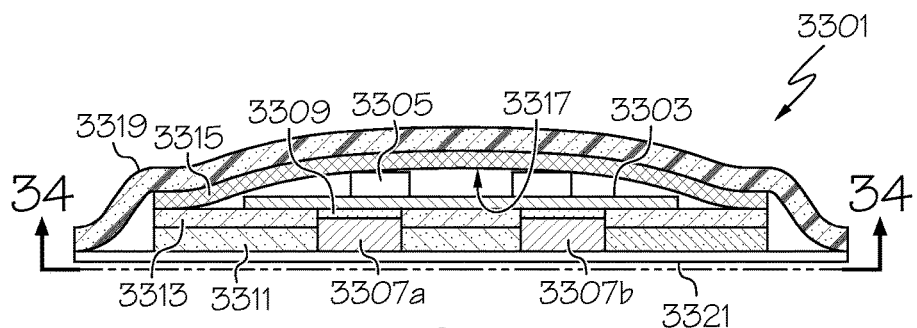
FIG. 33 is cross-sectional view of another example wireless sensor patch in accordance with aspects of the disclosure.

Methods of the disclosure can be modified to create a wide range of skin patches having similar, such as identical features to the wireless sensor patch 101 discussed above. FIGS. 33-39 schematically illustrate various features of alternative wireless sensor patches that, like the wireless sensor patch 101, include features that are not necessarily to scale for clarity. For instance, FIG. 33 is cross-sectional view of another example wireless sensor patch 3301. The wireless sensor patch 3301 can include a printed flexible circuit board 3303 that be provided with at least one electronic component, such as the illustrated plurality of various electronic components 3305 (e.g., silicon packaged electronic components), mounted to the printed flexible circuit board 3303. The flexible circuit board 3303 is designed to allow a certain amount of flexing to permit partial or entire conformance of the printed flexible circuit board 3303 to the skin surface 105 of the patient 103. As shown, the one or more electronic components 3305 extend from a first side of the printed flexible circuit board 3303 and may be selected in accordance with the desired characteristics of the sensor. For example, the electronic components 3305 may be provided to give the wireless sensor patch 3301 any one or combination of functional capabilities described with respect to the wireless sensor patch 101 above. In some examples, at least one electrode, such as the illustrated plurality of electrodes 3307a, 3307b, may be provided to extend from a second side of the printed flexible circuit board 3303. Various electrode configurations may be provided such as an Ag—AgCl electrode with an optional electrolyte gel. The one or more electrodes may be placed in operable communication with an electrical trace or other portion of an electrical circuit supported by the substrate of the printed flexible circuit board 3303. For example, a conductive coupling element 3309 may be used to fix the electrodes 3307a, 3307b to the appropriate location of the printed flexible circuit board 3303. In some examples, the conductive coupling element 3309 may comprise a conductive pressure sensitive adhesive and/or gel.

A skin-friendly adhesive patch 3311, similar or identical in composition to the skin-friendly adhesive patch 403 of the wireless sensor patch 3301 discussed above, may be mounted with respect to a second side of the printed flexible circuit board 3303. For example, as shown, a tie layer 3313 may mount the skin-friendly adhesive patch 3311 to the second side of the printed flexible circuit board 3303. The tie layer 3313 may comprise a double-coated breathable material or may simply comprise a double-sided adhesive tape.

In one example, the skin-friendly adhesive patch 3311 may comprise a hydrocolloid adhesive patch although other skin-friendly adhesives may be provided such as integrated hydrocolloid or other adhesives capable of absorbing moisture. For example, the skin-friendly adhesive patch 3311 can comprise a hydrocolloid such as the hydrocolloid material disclosed in any one of U.S. Pat. No. 7,335,416 that issued on Feb. 6, 2008, U.S. Pat. No. 6,710,100 that issued on Mar. 23, 2004, U.S. Pat. No. 6,583,220 that issued on Jun. 24, 2003, U.S. Pat. No. 6,326,421 that issued on Dec. 4, 2001, U.S. patent application Ser. No. 12/866,750 filed Aug. 9, 2010, and U.S. Provisional Patent 61/467,553 filed Mar. 25, 2011, which are herein incorporated by reference in their entireties.

Any of the wireless sensor skin patches discussed in the invention disclosure may include a cushion layer for patient comfort and/or to help protect the printed flexible circuit board (if provided) and/or protect other electrical components such as electrical components associated with the printed flexible circuit board. For example, as shown in FIG. 33, the wireless sensor patch 3301 can further include a cushion layer 3315 that may help protect the printed flexible circuit board 3303 and/or associated electronic components 3305 from damage. Indeed, the cushion layer 3315 may protect the circuit board and/or electronic components from externally applied forced (e.g., impact forces) that may otherwise damage the wireless sensor patch 3301. Moreover, the cushion layer 3315 may also enhance comfort to the patient wearing the patch or other individuals encountering the wireless sensor patch 3301. Indeed, rather than encounter relatively rigid electronic components 3305, the cushion layer 3315 may act as a protective bumper to avoid otherwise unpleasant encounters with the relatively rigid electronic components. In one example, the cushion layer 3315 may comprise a fabric represented by the cross-hatch pattern illustrated in the drawings. The illustrated fabric of the cushion layer 3315 comprises a nonwoven fabric although woven fabrics may be provided in further examples. The cushion layer 3315 may also include an adhesive applied to a surface 3317 facing the electronic components and printed circuit board. For example, the surface 3317 may be provided with a pressure sensitive adhesive that may facilitate mounting of the cushion layer 3315 in place by adhesive mounting to the electronic components 3305, printed flexible circuit board 3303 and/or tie layer 3313.

The wireless sensor patch 3301 can further include a flexible cover patch 3319 mounted with respect to the skin-friendly adhesive patch 3311 with the electronic component 3305 positioned within a space between the flexible cover patch 3319 and the skin-friendly adhesive patch 3311. As shown, the flexible cover patch 3319 can be positioned over the cushion layer 3315 such that the cushion layer 3315 is positioned to extend between the electronic component 3305 and the flexible cover patch 3319. The flexible cover patch 3319 may comprise a polymeric member, such as a closed cell foam material that may be substantially water resistant yet breathable to help protect the electrical components 3305 and the printed flexible circuit board 3303.

Figure 34:
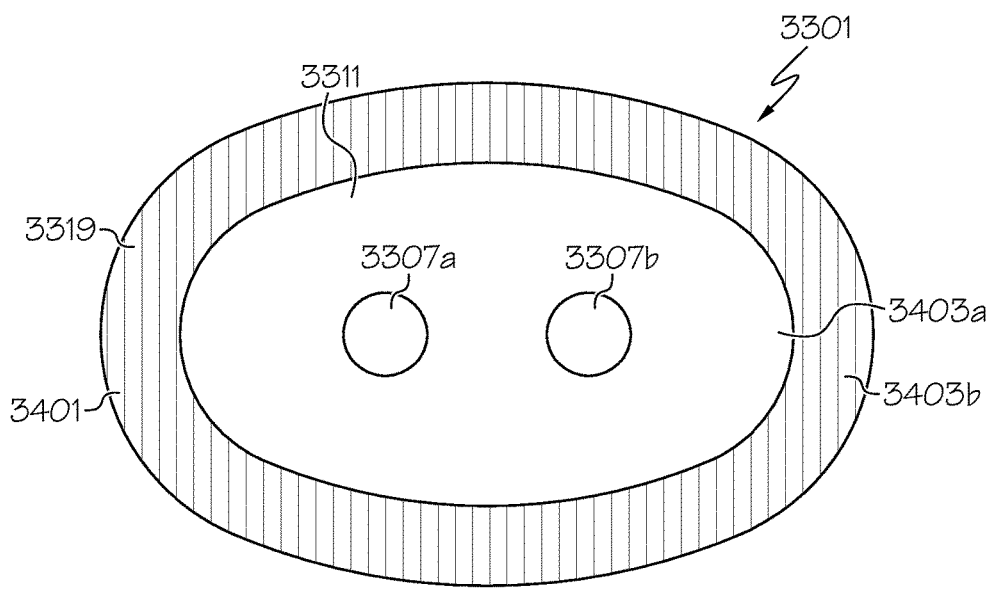
FIG. 34 is a bottom view of the wireless sensor patch of FIG. 33 along line 34-34 of FIG. 33, wherein the release liner is not illustrated for clarity.

FIG. 34 is a bottom view of the wireless sensor patch 3301 wherein a release liner 3321, designed to preserve the adhesive surfaces from contamination prior to application, is not illustrated for clarity. As represented by the vertical lines set forth in FIG. 34, the flexible cover patch 3319 may also include an adhesive layer 3401 designed to mount the flexible cover patch 3319 to the cushion layer 3315. The adhesive layer 3401 can comprise a pressure sensitive adhesive such as rubber-based adhesive, acrylic adhesive or silicone adhesive that allows a peripheral adhesive portion 3403*b* defined by an adhesive layer 3401 of the flexible cover patch 3319 to immediately adhere to the skin surface 105 upon application of the wireless sensor patch 3301. Moreover, as mentioned previously, the wireless sensor patch 3301 can comprise the skin-friendly adhesive patch 3311.

As shown in FIG. 34, the peripheral adhesive portion 3403*b* at an outer periphery of the adhesive layer 3401 can circumscribe a skin-friendly portion 3403*a* of the skin-friendly adhesive patch 3311. Indeed, as apparent in FIGS. 33-39, the flexible cover patch of the wireless skin patch can have a footprint that is larger than a foot print of the skin-friendly adhesive patch. As such, each wireless skin patch of the present disclosure can include an adhesive footprint with a skin-friendly adhesive portion defined by the skin-friendly adhesive patch that is optionally circumscribed by a peripheral adhesive portion defined by an adhesive layer of the flexible cover patch. For instance, by way of illustration, FIG. 34 illustrates an adhesive footprint of the wireless skin patch 3301 with the skin-friendly portion 3403*a* defined by the skin-friendly adhesive patch 3311 that is circumscribed by the peripheral adhesive portion 3403*b* defined by an adhesive layer 3401 of the flexible cover patch 3319.

As such, an outer peripheral adherence of the wireless sensor patch 3301 to the skin surface 105 of the patient 103 may be achieved. At the same time, the skin-friendly adhesive patch 3311 may be held in place against the skin surface 105 to allow sufficient time for the skin-friendly adhesive patch 3311 to cure into an effective adhesive member. The skin-friendly adhesive patch 3311 allows the wireless sensor patch 3301 to be applied to the skin surface for a significant length of time without aggravating the skin surface when compared to the adhesive layer 3401. At the same time, a relatively small peripheral portion 3403*b* of the adhesive layer 3401 may allow the peripheral portions of the patch to be immediately adhered to the skin surface while allowing the skin-friendly portion 3403*a* of the skin-friendly adhesive patch 3311 sufficient time to cure.

Figure 35:
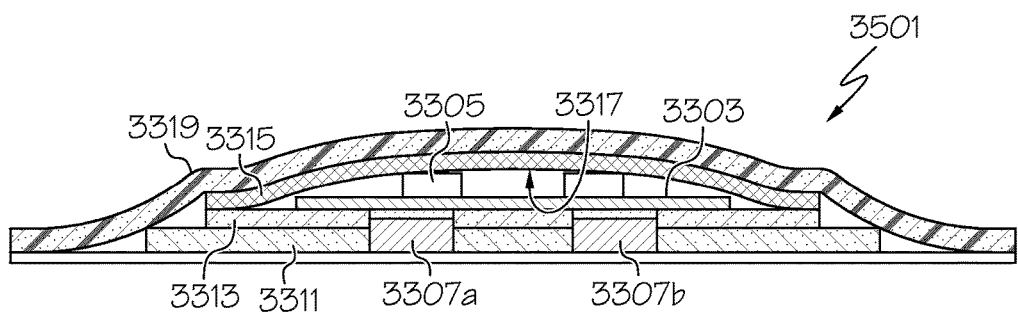
FIG. 35 is cross-sectional view of still another example wireless sensor patch in accordance with aspects of the disclosure.

FIG. 35 is cross-sectional view of still another example wireless sensor patch 3501 in accordance with additional aspects of the disclosure. Unless otherwise indicated, the wireless sensor patch 3501 can include identical or similar features discussed with respect to the wireless sensor patch 3301 discussed above and referenced in FIGS. 33-34. Referring to FIGS. 33-35, the footprint of the wireless sensor patch 3501 shown in FIG. 35 is larger than the footprint of the wireless sensor patch 3301 illustrated in FIGS. 33-34. In such applications, the footprints of the skin-friendly adhesive patch 3311 and/or flexible cover patch 3319 of the wireless sensor patch 3501 can likewise be greater than the corresponding footprints of the skin-friendly adhesive patch and/or flexible cover patch of the wireless sensor patch 3301. As illustrated, the footprint of the skin-friendly adhesive patch can be increased with an increase in the overall footprint of the wireless sensor patch to provide a more skin-friendly adhesive patch that exposes a greater portion of the skin to the skin-friendly adhesive.

Figure 36:
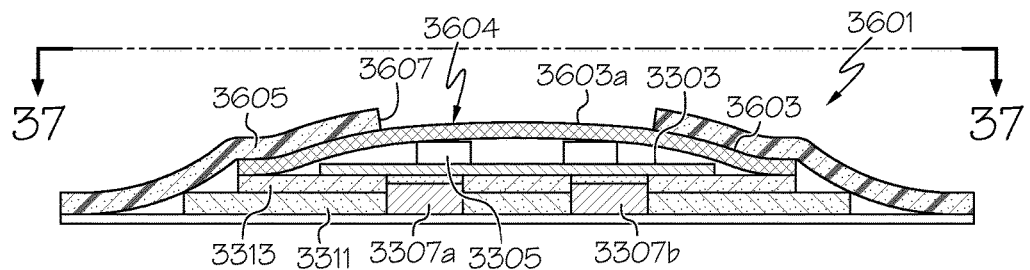
FIG. 36 is cross-sectional view of yet another example wireless sensor patch in accordance with aspects of the disclosure.
Figure 37:
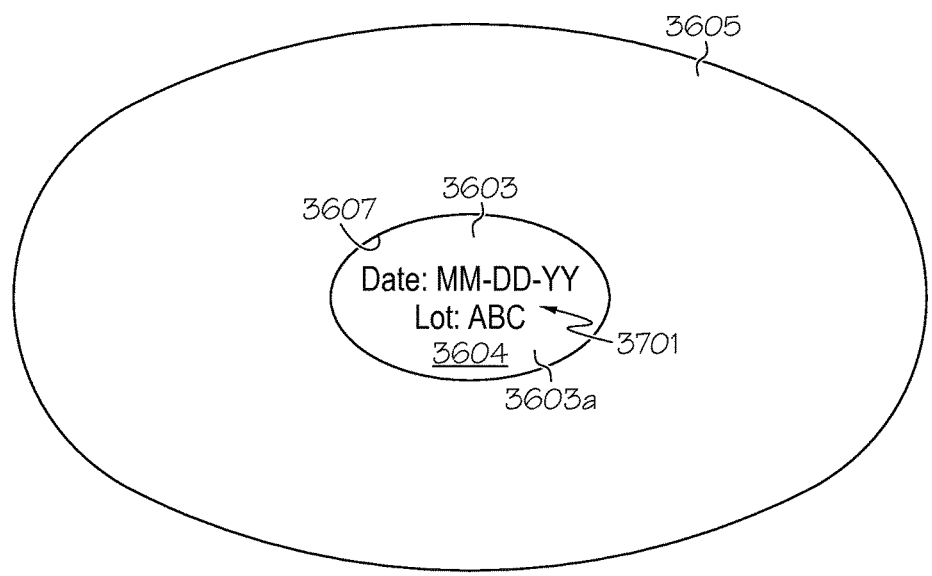
FIG. 37 is a top view of the wireless sensor patch of FIG. 36 along line 37-37 of FIG. 36.

FIG. 36 is cross-sectional view of yet another example wireless sensor patch 3601 in accordance with aspects of the disclosure. Unless otherwise indicated, the wireless sensor patch 3601 can include identical or similar features discussed with respect to the wireless sensor patches 3301, 3501 discussed above and referenced in FIGS. 33-35. However, as shown, the cushion layer 3603 of the wireless sensor patch 3601 may comprise a foam cushion material or other material that will allow indicia 3701 (see FIG. 37) to be printed on an outer surface 3604 of the cushion layer 3603. In such examples, as shown in FIGS. 36 and 37, the flexible cover patch 3605 may define a viewing port 3607 configured to permit viewing of a portion 3603a the cushion layer 3603 through the viewing port 3607 of the flexible cover patch 3605. In some examples, indicia 3701, such as identifying information, may be printed on the portion 3603a of the cushion layer 3603 and viewed through the viewing port 3607 defined by the flexible cover patch 3605. In some examples, the viewing port 3607 may comprise an aperture although a translucent or transparent membrane or other port allowing viewing may be provided in further examples. The flexible cover patch of any of the example wireless sensor patches of the disclosure may include a view port to allow viewing of indicia underlying the flexible cover patch. For example, any of the flexible cover patches of any of the example wireless sensor patches may include a view port comprising an aperture allowing viewing of indicia printed on a surface (e.g., a surface of a cushion layer) that would otherwise be obscured by the flexible cover patch.

Figure 38:
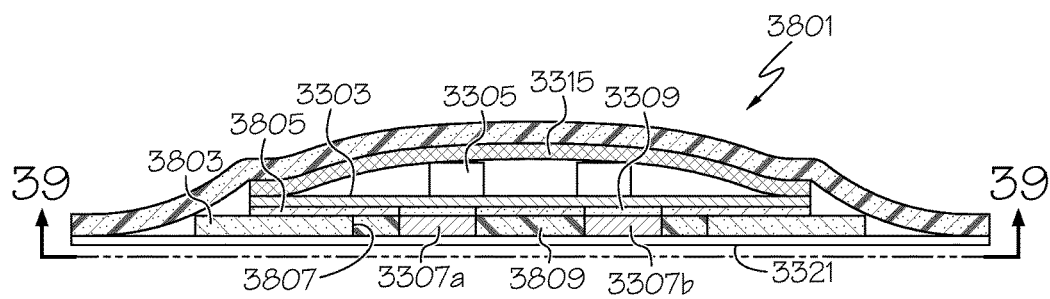
FIG. 38 is cross-sectional view of another example wireless sensor patch in accordance with aspects of the disclosure.

FIG. 38 is cross-sectional view of yet another example wireless sensor patch 3801. The wireless sensor patch 3801 can include a printed flexible circuit board 3303 that be provided with various previous-described electronic components 3305. At least one electrode, such as the illustrated plurality of electrodes 3307a, 3307b may extend from the second side of the printed flexible circuit board 3303. As mentioned previously, the electrodes may comprise Ag—AgCl electrodes that may optionally include electrolyte gel and may be placed in operable communication with an electrical trace or other portion of an electrical circuit supported by the substrate of the printed flexible circuit board 3303. For example, a conductive coupling element 3309 may be used to fix the electrodes 3307a, 3307b to the appropriate location of the printed flexible circuit board 3303. For instance, the conductive coupling element 3309 may comprise a conductive pressure sensitive adhesive and/or gel. A skin-friendly adhesive patch 3803, similar or identical in composition to the skin-friendly adhesive patches 403, 3311 discussed above, may be mounted with respect to the printed circuit board 3303 by way of a tie layer 3805. The tie layer 3805 may comprise the illustrated double-sided adhesive tape although other tie layers (e.g., the tie layer 3313 discussed above) may be used in further examples.

Figure 39:
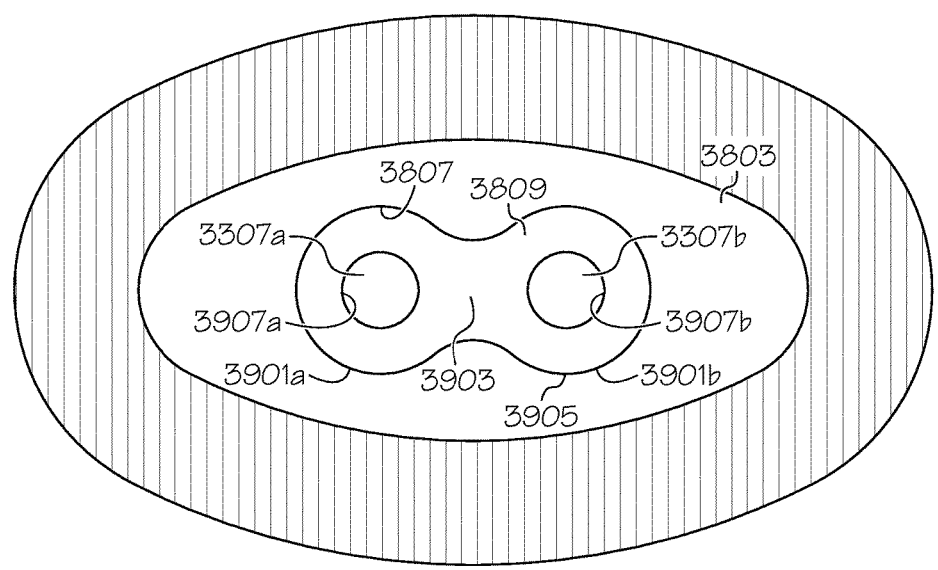
FIG. 39 is a bottom view of the wireless sensor patch of FIG. 38 along line 39-39 of FIG. 38, wherein the release liner is not illustrated for clarity.

In any of the example wireless skin patched described through the disclosure, any of the wireless skin patches including one or more electrodes (e.g., electrodes 3307a, 3307b) may include an optional electrode insulation member. For example, as illustrated in FIGS. 38 and 39, an electrode insulation member 3809 may be positioned within at least one through aperture 3807. Although a single aperture 3807 is shown, a plurality of apertures 3807 may be provided in further examples wherein at least one of the apertures includes an electrode insulation member 3809. The electrode insulation member 3809 can circumscribe at least one electrode to prevent contact between the circumscribed electrode and the skin-friendly adhesive patch 3803. For example, as shown, the electrode insulation member 3809 may circumscribe both of the electrodes 3307a, 3307b although the electrode insulation member 3809 may circumscribe a single electrode or less than all of a plurality of electrodes in further examples. In some examples, the electrode insulation member 3809 is designed to electrically insulate the electrodes 3307a, 3307b from one another or other components. In one example, the electrode insulation member can comprise a closed-cell foam, nonwoven fabric or other material configured to electrically insulate one or more of the electrodes. Electrical insulation can be particularly beneficial since the skin-friendly adhesive patch 3803 will tend absorb significant levels of liquid (e.g., water) from the skin surface 105 of a patient 103 over time. The electrode insulation member 3809 can prevent direct exposure of the electrodes 3307 to the skin-friendly adhesive patch 3803, thereby avoiding undesired electrical communication (e.g., short circuiting) of the electrodes 3307a, 3307b that may otherwise occur through the saturated skin-friendly adhesive patch 3803.

In one example, the electrodes may extend through an aperture of the electrode insulation member 3809. For instance, as shown in FIG. 39, the first electrode 3307a may extend through a first aperture 3907a of the electrode insulation member 3809 while the second electrode 3307b may extend through the second aperture 3907b. As such, in some examples each electrode 3307a, 3307b can extend through a single through aperture 3807 of the skin-friendly adhesive patch 3803 while extending through corresponding apertures 3907a, 3907b of the electrode insulation member 3809. In such an example, the electrode insulation member 3809 can therefore prevent both the first electrode 3307a and the second electrode 3307b from contacting the skin-friendly adhesive patch 3803. Insulating both electrodes can help further electrically insulate the electrodes from one another and/or from other components. Although not shown, the electrode insulation member may be provided to insulate a single electrode. Insulating a single electrode may reduce material costs, increase available skin-friendly adhesive surface area contact with the skin while still electrically insulating the insulated electrode from the remaining electrode(s).

As further shown in FIG. 39, the electrode insulation member 3809 can optionally comprise bulbous portions 3901a, 3901b having a footprint larger than the corresponding footprint of the electrodes 3307a, 3307b to allow the electrode insulating member to circumscribe each of the electrodes. Moreover, a reduced neck portion 3903 may be provided between the bulbous portions 3901a, 390b such that the outer periphery 3905 of the electrode insulation member 3809 together with the apertures 3907 provides the electrode insulation member 3809 as an 8-shaped electrode insulation member having a shape of the number "8". Providing the reduced neck portion 3903 allows the bulbous portions to be connected together while still maximizing the surface area of the skin-friendly adhesive available for contacting the skin surface. Still further, the reduced neck portion can help increase the electrical insulation properties in the area positioned between the electrodes, thereby enhancing thermal insulation characteristics while maximizing the surface area of the skin-friendly adhesive available for contacting the skin surface. Although not shown, the bulbous portions 3901 may simply comprise donuts that are not connected to one another. In such an example, a single donut may be provided about a single electrode to electrically insulate a selected electrode from the other electrode(s) and/or other components. Alternatively, a plurality of donuts may be provided, for example, about each electrode to electrically insulate all of the electrodes from one another and/or other components.

The inventors hereby state their intent to rely on the Doctrine of Equivalents to determine and assess the reasonably fair scope of their invention as it pertains to any apparatus, system, method or article not materially departing from but outside the literal scope of the invention as set out in the following claims.

What is claimed is:

1. A method of manufacturing a plurality of wireless sensor patches comprising the steps of:
   (I) unwinding a skin-friendly adhesive membrane from a skin-friendly adhesive membrane storage roll, wherein the skin-friendly adhesive membrane includes a substrate sheet carrying a layer of skin-friendly adhesive and a first release liner, wherein the first release liner is carried by the layer of skin-friendly adhesive, wherein the layer of skin-friendly adhesive is sandwiched between the first release liner and the substrate sheet;
   (II) kiss cutting through the substrate sheet and the skin-friendly adhesive down to the first release liner to define a skin-friendly adhesive patch;
   (III) unwinding a flexible support membrane from a support membrane storage roll, wherein the flexible support membrane includes a flexible support sheet with a skin adhesive layer applied to a first face of the flexible support sheet and a second release liner, wherein the second release liner is carried by the skin adhesive layer with the skin adhesive layer being sandwiched between the second release liner and the flexible support sheet;
   (IV) kiss cutting through the flexible support sheet and the skin adhesive layer to the second release liner to define an opening extending through the flexible support sheet and the skin adhesive layer;
   (V) removing the second release liner to expose the skin adhesive layer;
   (VI) laminating the substrate sheet to the flexible support sheet with the skin adhesive layer of the flexible support membrane;
   (VII) unwinding a tie layer membrane from a tie layer membrane storage roll, wherein the tie layer membrane includes a tie layer carrying a third release liner;
   (VIII) kiss cutting through the tie layer to the third release liner to define a tie layer patch;
   (IX) laminating the tie layer patch to the flexible support sheet;
   (X) cutting at least one probe opening through the tie layer membrane in alignment with the opening defined during step (IV);
   (XI) removing the third release liner to expose the tie layer patch, wherein the tie layer is laminated to the flexible support sheet;
   (XII) mounting a sensor device with respect to the flexible support membrane with a sensor probe in alignment with corresponding openings defined during steps (IV) and (X);
   (XIII) unwinding a flexible cover membrane from a flexible cover membrane storage roll;
   (XIV) forming a pocket within the flexible cover membrane;
   (XV) cutting the flexible cover membrane to define a flexible cover patch including the pocket;
   (XVI) laminating the flexible cover patch to the tie layer patch with the sensor device being at least partially received in the pocket; and
   (XVII) cutting a portion of the flexible support sheet and the skin adhesive layer to provide a wireless sensor patch.

2. The method of claim 1, wherein the step (XVII) provides an outer periphery of the skin adhesive layer circumscribing the skin-friendly adhesive patch.

3. The method of claim 1 wherein the skin-friendly adhesive comprises a hydrocolloid skin adhesive.

4. The method of claim 1, wherein the flexible support membrane comprises a fabric.

5. The method of claim 4, wherein the fabric comprises a nonwoven fabric.

6. The method of claim 1, wherein the step (XVII) is performed periodically to sequentially produce a plurality of wireless sensor patches.

7. The method of claim 1, further comprising a step of providing indicia to a portion each wireless sensor patch containing information that matches information of indicia provided on a corresponding package housing each wireless sensor patch.

8. The method of claim 7, further comprising a step of associating the indicia of the portion of the wireless sensor patch with a batch of at least one source of assembly materials used to manufacture the wireless sensor patch.

* * * * *